United States Patent [19]
Haynes et al.

[11] Patent Number: 5,310,946
[45] Date of Patent: May 10, 1994

[54] CYCLIC PEROXYACETAL LACTONE, LACTOL AND ETHER COMPOUNDS

[75] Inventors: Richard K. Haynes, Eastwood; Simone C. Vonwiller, North Ryde, both of Australia

[73] Assignee: Rhone-Poulenc Rorer S.A., Antony Cedex, France

[21] Appl. No.: 842,413

[22] PCT Filed: Sep. 27, 1990

[86] PCT No.: PCT/AU90/00456
§ 371 Date: Mar. 26, 1992
§ 102(e) Date: Mar. 26, 1992

[87] PCT Pub. No.: WO91/04970
PCT Pub. Date: Apr. 18, 1991

[30] Foreign Application Priority Data
Sep. 27, 1989 [AU] Australia ............... PJ6595

[51] Int. Cl.$^5$ ............... C07D 311/78; C07D 323/00; C07C 69/73
[52] U.S. Cl. ............... 549/276; 549/281; 549/350; 560/183
[58] Field of Search ............... 560/183; 549/350, 276, 549/781

[56] References Cited
U.S. PATENT DOCUMENTS
4,992,561  2/1991  Roth et al. ............... 549/279

FOREIGN PATENT DOCUMENTS
91/01832  3/1991  PCT Int'l Appl. ........ C07D 493/10

OTHER PUBLICATIONS
"A simple Conversion of Artesmisinic Acid Into Artemisinin," Roth et al., Journal of Natural Products, vol. 52, pp. 1183–1185, Oct. 1989.
"A Short and Stereospecific Synthesis of (+)-Deoxoartemisinin and (−)-Deoxodesoxyartemisinin," Jung et al., Tetrahedron Ltrs., vol. 30, pp. 5973–5976, Nov. 1989.
"Catalysed Oxygenation of Allylic Hydroperoxides Derived From Qinghao . . . " Haynes et al., J. Chem. Soc. Commun., p. 451 Feb. 1990.
(List continued on next page.)

*Primary Examiner*—C. Warren Ivy
*Assistant Examiner*—A. A. Owens
*Attorney, Agent, or Firm*—Dressler, Goldsmith, Shore & Milnamow, Ltd.

[57] ABSTRACT

A process for preparing a compound containing (a) peroxyacetal lactone, (b) peroxyacetal lactol or (c) peroxycacetal ether functionality comprising oxygenating in the presence of one or more oxidizing metal catalysts a compound containing (i) hydroperoxy alkene carboxylic acid, (ii) hydroperoxy alkene aldehyde, (iii) hydroperoxy alkene keto, (iv) hydroperoxy alkene alcohol functionality or (v) dialkyl acetals of compounds in (ii) and (iii) above. For example (I)→(II) wherein n=1,2 or 3; m=0, 1, 2,; p=0, 1, 2 or 3; $R^5$=—COOH, —C-(O)R, —CROH, (α), where R is H, alkyl, aryl or arylalkyl; $R^1$ are independently alkyl, arylalkyl or each $R^1$ together with the group —O—C—O— to which they are attached form a cyclic acetal; X=CR$^2$R$^3$, O, S, SO, SO$_2$ where $R^2$ and $R^3$ are independently selected from H, optionally substituted alkyl, optionally substituted aryl, and wherein when n>1, X is independently selected and can be branched or straight chain and X together with a substituent Y can also form a ring; Y is a substituent selected from H; optionally substituted alkyl or aryl; Y can be on the same C atom as the hydroperoxy group and an y C atom may be disubstituted by Y and includes replacement of H atom(s) in "(CH$_2$)$_m$" by Y; $R^6$ or R $^7$ is as defined for R above, H, OH, OR$^1$ or together with the carbon atom to which they are attached form a keto group. The present invention is particularly important in its application to the preparation of biologically active compounds comprising the cyclic peroxyacetal lactone or lactol functionalities. One such biologically active compound is qinghaosu (Artemisinin).

15 Claims, No Drawings

OTHER PUBLICATIONS

"Stereospecific Synthesis of (+)-Homodeoxoartemisinin," Heterocycles, vol. 29, No. 12, 1989, pp. 2273-2277.

"Artemisinic Acid: A Versatile Chiral Synthon and Bioprecursor to Natural Products," Jung et al., Planta Med. 56(1990), p. 624.

"A Concise and Stereoselective Synthesis of (+)-n-Butyldeoxoartemisinin," Jung et al., Synlett, 1990, pp. 743-744.

"The Development of New Peroxidic Antimalarials," Haynes et al., Chemistry in Australia, Mar. 1991, pp. 64-67.

"A Facile Semi-Synthesis of the Antimlarial Drug Qinghaosu," Roth et al., Journal of Chem. Education, pp. 612-613 Jul. 1991.

"A Concise Synthesis of 12-(3'-Hydroxy-n-Propyl)-Deoxoartemisinin," Jung et al. Bioorganic & Medicinal Chemistry Ltrs., 1991, vol. 1, No. 12, pp. 741-744.

"1,2-Dioxetanes as New Antimalarial Agents," Zaman et al., J. Chem. Soc. Chem. Commun., 1992, p. 329.

"Efficient Preparation of Novel Qinghaosu (Artemisinin) Derivatives," Haynes et al., Synlett, 1992.

"Practical Conversion of Artemisinic Acid into Deoxyartemisinin," Jung et al., J. Org. Chem., 1986, 51, No. 26, 1985, pp. 5417-5419.

"Total Synthesis of Arteanuuin (Qinghaosu) and Related Compounds," Zhou, Pure and Applied Chemistry, 58, No. 5, 1986, pp. 817-824.

CYCLIC PEROXYACETAL LACTONE, LACTOL AND ETHER COMPOUNDS

TECHNICAL FIELD

This invention relates to a new process for preparing cyclic peroxyacetal lactone, lactol or ether compounds.

BACKGROUND OF THE INVENTION

The present invention is particularly important in its application to the preparation of biologically active compounds comprising the cyclic peroxyacetal lactone or lactol functionalities.

One such biologically active compound is qinghaosu (Artemisinin) which has the following formula:

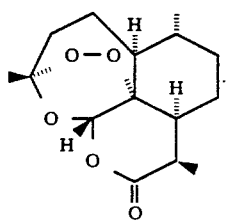

Qinghaosu is a potent antimalarial which has been successfully used to treat patients suffering from malaria. The reemergence of strains of malaria resistant to conventional (chloroquine) therapy is posing a worldwide problem, and indeed, there is no universally acceptable cure at the present time. Qinghaosu occurs to the extent of about 0.1 (dry weight) in an annual shrub, qinghao or (*Artemisia annua*), which grows in most provinces of China. Unfortunately, the world demand for qinghaosu far exceeds the supply, and there is considerable pressure to develop bioactive analogues, or to develop alternative sources for the compound. The compound has been prepared by total synthesis in the laboratory, but the structural complexity is such that no total laboratory synthesis has been economically feasible.

The Disclosure of the Invention

In one aspect, the invention provides a process for preparing a compound containing:
a) peroxyacetal lactone
b) peroxyacetal lactol or
c) peroxyacetal ether functionality
comprising oxygenating a compound containing:
i) hydroperoxy alkene carboxylic acid
ii) hydroperoxy alkene aldehyde
iii) hydroperoxy alkene keto or
iv) hydroperoxy alkene alcohol functionality
v) dialkyl acetals of compounds in ii) and iii) above
in the presence of one or more oxidizing metal catalysts.

The process of the present invention can be carried out as a "one-pot" reaction, referred to as the direct method or by a series of steps, referred to as the indirect method.

In particular, the direct method involves oxygenation of a compound of formula

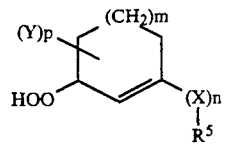

in the presence of one or more oxidizing metal catalysts to give a compound of formula

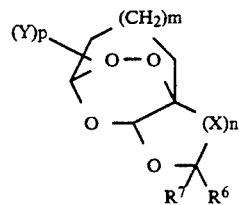

wherein
n = 1, 2 or 3
m = 0, 1, or 2,
p = 0, 1, 2 or 3
$R^5$ = —COOH, —C(O)R, —CROH,

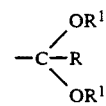

where R is H, alkyl, aryl or arylalkyl $R^1$ are independently alkyl, aryl or each $R^1$ together with the group —O—C—O— to which they are attached form a cyclic acetal X = $CR^2R^3$, C=$CR^2R^3$, O, S, SO or $SO_2$ where $R^2$ and $R^3$ are independently selected from H, optionally substituted alkyl, optionally substituted aryl, the optional substituents being selected from alkyl, aryl, halogen, OR, $CF_3$, $NO_2$, COR, NRR′, SR, COOR, CONRR′, $SO_3R$, $SO_2NRR'$, SR, SOR and $SO_2R$, where R and R′ are as defined for R above; SR″, SOR″, $SO_2R''$ where R″ is alkyl or aryl optionally substituted by one or more substitutents selected from alkyl, aryl, halogen, OR, $CF_3$, $NO_2$, COR, NRR′, SR, COOR, CONRR′, $SO_3R$, $SO_2NRR'$, SR, SOR and $SO_2R$, where R and R′ are as defined for R above; and wherein when n > 1, X is independently selected and can be branched or straight chain and X together with a substituent Y can also form a ring;

Y is a substituent selected from H; alkyl or aryl optionally substituted by one or more sustituents selected from alkyl, aryl, halogen, OR, $CF_3$, $NO_2$, COR, NRR′, SR, COOR, CONRR′, $SO_3R$, $SO_2NRR'$, SR, SOR and $SO_2R$, where R and R′ are as defined for R above; Y can be on the same C atom as the hydroperoxy group and any C atom may be disubstituted by Y and includes replacement of H atom(s) in "$(CH_2)_m$" by Y;

$R^6$ or $R^7$ is as defined for R above, H, OH, $OR^1$ or together with the carbon atom to which they are attached form a keto group.

The direct method involves oxygenation of the hydroperoxy compound in the presence of one or more catalysts to undergo a new oxygenation-cleavage-cyclization reaction to give a cyclic peroxyacetal lactone, lactol or ether compound.

According to IUPAC nomenclature, acetals derived from acids, ketones, aldehydes are all called "acetals". However, it is common to name an acetal derived from a ketone, a "ketal". Thus, it is to be understood that the term "acetal" also includes within its scope acetals derived from ketones i.e. ketals.

The skilled addressee would understand that the process of the invention may result in one or more stereogenic (chiral) centres being formed resulting in stereoisomers. Thus, it is to be understood that the present invention includes within its scope the preparation of stereoisomers. The present invention also encompasses any isomers or mixtures thereof when prepared according to the present invention.

The Schematic Diagram (A) illustrates the process for the direct method, starting from a cyclic hydroperoxy alkene carboxylic acid, aldehyde, ketone, alcohol, aldehyde acetal and ketone acetal respectively.

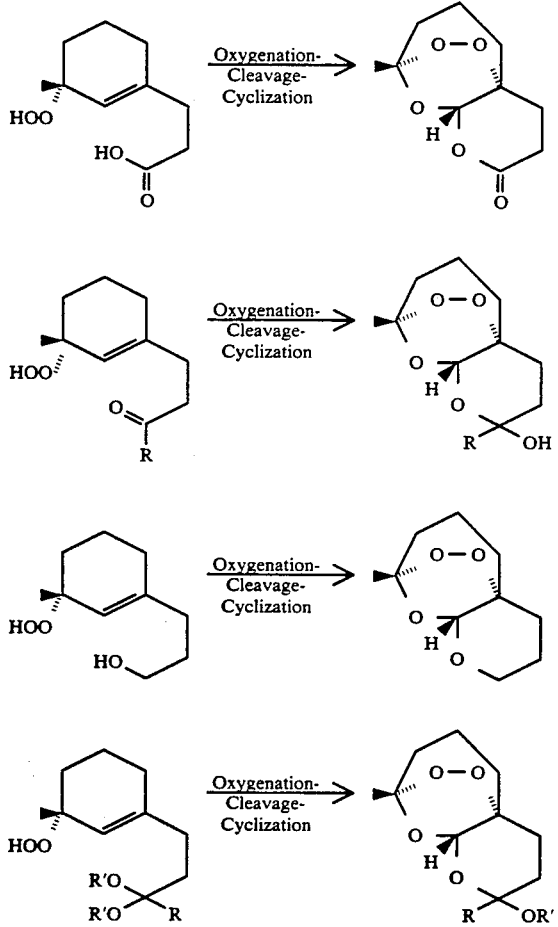

NB: In this Scheme, one enantiomer only of each chiral compound is depicted. There is also poduced an equal amount of the other enantiomer in each case.

The indirect method involves an esterification of the hydroperoxide to give a new intermediate hydroperoxide followed by treatment with one or more catalysts in the presence of oxygen to undergo a new oxygenation-cleavage reaction and subsequent cyclization to give a cyclic peroxyacetal lactone.

Thus, in another aspect of the invention there is provided a process for preparing a peroxyacetal lactone compound of formula

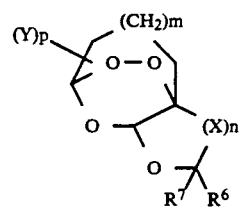

comprising;
i) esterifying a compound of formula

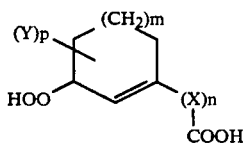

to give a compound of formula

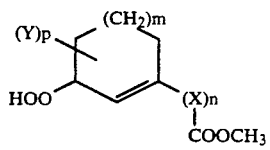

ii) oxygenation in the presence of one or more oxidizing metal catalysts to give compounds of formula

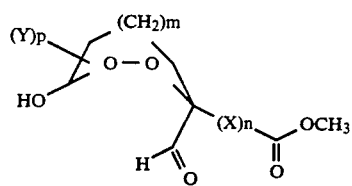

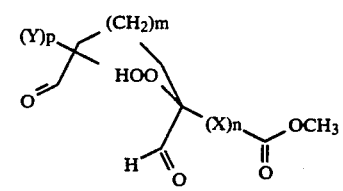

followed by
iii) treatment with a protic acid or lewis acid to give the desired cyclic peroxy acetal lactone compound;
where $m, n, p, X, Y, R^6$ and $R^7$ are as defined above.

The following Schematic Diagram (B) illustrates the process for the indirect method, starting from a cyclic hydroperoxy alkene carboxylic acid.

SCHEMATIC DIAGRAM (B)
INDIRECT METHOD
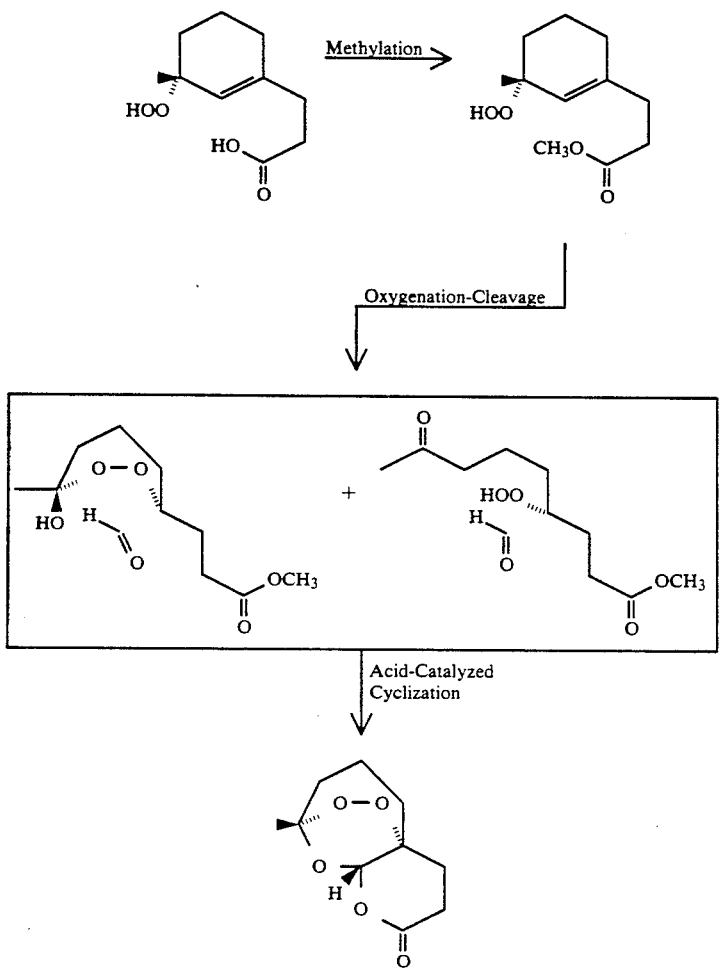
NB: In this Scheme one enantiomer only of each chiral compound is depicted. There is also produced an equal amount of the other enantiomer in each case.
Preferably, the starting hydroperoxide compound is obtained by oxygenation of the corresponding alkene compounds as follows:
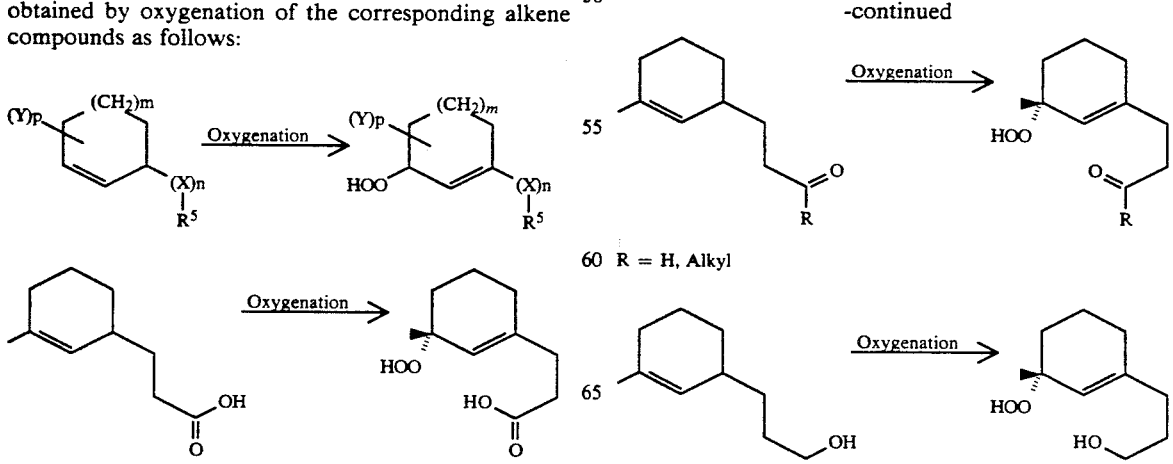
R = H, Alkyl

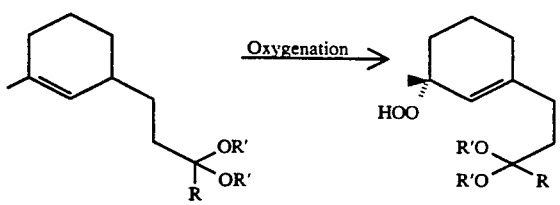

R = H, Alkyl
R' = Alkyl

NB: In this Scheme, one enantiomer only of each chiral compound is depicted. There is also produced an equal amount of the other entantiomer in each case.

Preferably, the alkene carboxylic acid has an alkyl or other substituent on the double bond and an optionally substituted alkyl chain between the alkene group and the carboxyl group. The alkyl chain preferably contains two, four or more carbon atoms and may also contain one or more heteroatoms such as oxygen. The alkene carboxylic acid may be cyclic or acyclic. The process is preferably carried out as a "one-pot" reaction.

The present invention is particularly suitable for preparing qinghaosu.

According to the process of the invention, the starting material for preparing qinghaosu, comprising the alkene carboxylic acid functionalities is preferably qinghao acid (artemisinic acid or arteannuic acid) of the following formula:

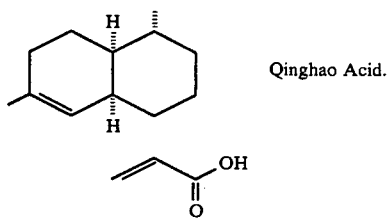

Qinghao Acid.

Qinghao acid occurs to the extent of 1-3% (dry weight) in *Artemisia annua*, which is much greater than the natural occurrence of qinghaosu and is easily extracted from the plant. There have been several attempts carried out elsewhere to convert this compound into qinghaosu, but none is preparatively useful.

Thus, in another aspect of the invention there is provided a process for converting qinghao acid into qinghaosu comprising
i) reducing qinghao acid to give dihydroqinghao acid of formula

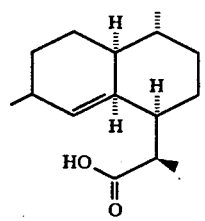

Dihydroqinghao acid ii) oxygenating dihydroqinghao acid to give the corresponding hydroperoxides and without isolation iii) oxgenating in the presence of one or more oxidising metal catalysts to give qinghaosu.

In a further aspect of the invention there is provided a process for converting qinghao acid into qinghaosu comprising
i) reducing qinghao acid to give dihydroqinghao acid;
ii) oxygenating dihydroqinghao acid followed by methylation to give the methyl ester hydroperoxide of formula

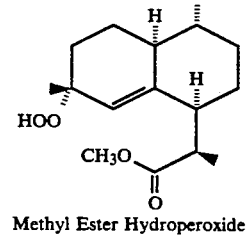

Methyl Ester Hydroperoxide iii) oxygenation in the presence of one or more oxidizing metal catalysts to give intermediate products of formulae

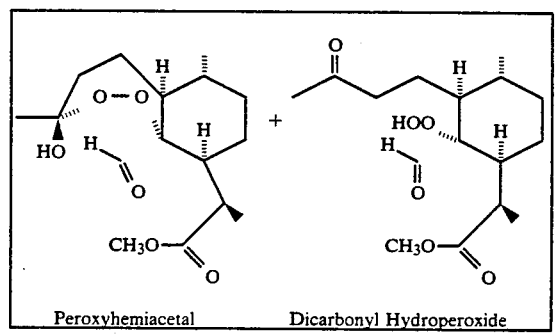

Peroxyhemiacetal    Dicarbonyl Hydroperoxide and with or without isolation
iv) treatment with protic or Lewis acid catalyst to give qinghaosu.

The process of the invention will now be described in more detail in relation to the preparation of qinghaosu.

However, it will be understood, that the invention is not limited to this preparation.

BEST MODE OF CARRYING OUT THE INVENTION

In detail, the process of the invention can be applied to conversion of qinghao acid into qinghaosu according to the direct method as illustrated in the following Schematic Diagram (C).

SCHEMATIC DIAGRAM (C)
Direct Method for Conversion of Qinghao Acid into Qinghaosu (Artemisinin)

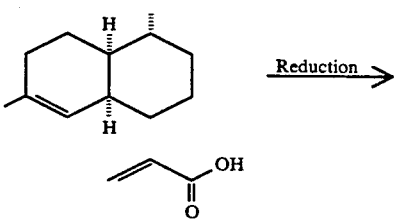

Qinghao Acid

-continued
SCHEMATIC DIAGRAM (C)
Direct Method for Conversion of Qinghao Acid into Qinghaosu (Artemisinin)

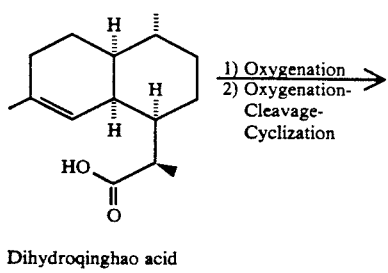

Dihydroqinghao acid

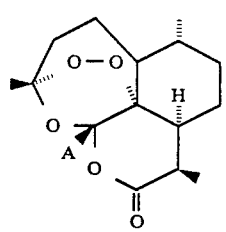

Qinghaosu

Firstly, qinghao acid is reduced by known methods to give dihydroqinghao acid. This acid is then converted by oxygenation into the new hydroperoxides. Without isolation, the mixture is treated with one or more metal complex catalysts under an oxygen atmosphere and undergoes the new oxygenation-cleavage-cyclization reaction to give qinghaosu.

The preparation of qinghaosu can be carried out according to the indirect method as illustrated in Schematic Diagram (D).

SCHEMATIC DIAGRAM (D)
Indirect Method for Conversion of Qinghao Acid into Qinghausu.

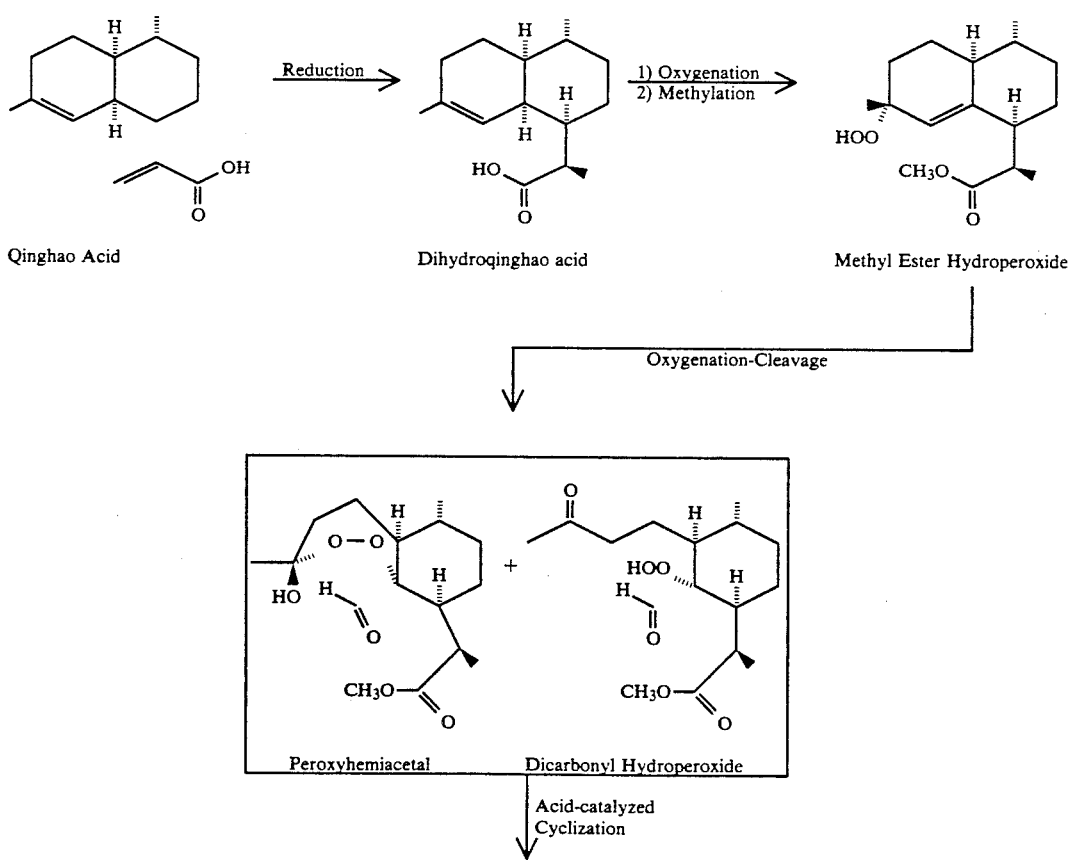

-continued
SCHEMATIC DIAGRAM (D)
Indirect Method for Conversion of Qinghao Acid into Qinghausu.

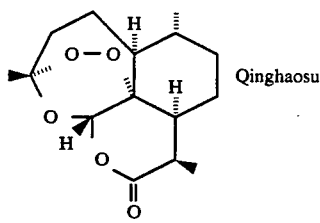

Qinghaosu

Firstly, qinghao acid is reduced by known methods to give dihydroqinghao acid. This acid is then converted by oxygenation into the corresponding carboxylic acid hydroperoxides which are then methylated to give the corresponding tertiary hydroperoxide and its regioisomer. The major tertiary hydroperoxide is then treated with one or more metal complex catalysts under an oxygen atmosphere and undergoes the new oxygen-cleavage reaction to give the corresponding peroxyhemiacetal and the hydroperoxide. These compounds are then cyclized through acid catalysis to give qinghaosu.

Alternatively, the above process can be carried out without first reducing qinghao acid into dihydroqinghao acid, in which case, a compound known as dehydroqinghaosu (artemisitene) is produced.

Without the reduction step, the direct method results in a "one-pot" reaction as illustrated in Schematic Diagram (E).

SCHEMATIC DIAGRAM (E)
Direct Method for the Conversion of Qinghao Acid into Dehydroqinghaosu (Artemisitene).

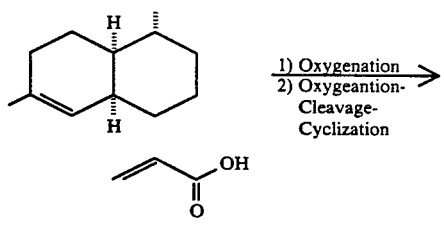

1) Oxygenation
2) Oxygeantion-
   Cleavage-
   Cyclization

Qingghao Acid

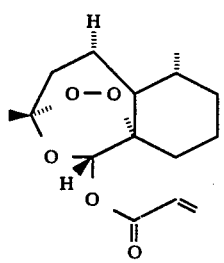

Dehydroqinghaosu

Qinghao acid is converted by oxygenation into the hydroperoxides and without isolation, the mixture is treated as described above from the direct method to give dehydroqinghaosu.

By-products of this reaction, not formed in the reaction of the indirect method are new keto-aldehydes of formulae

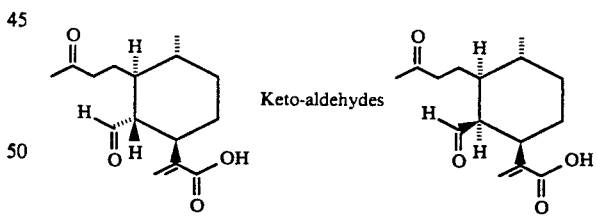

Keto-aldehydes

The indirect method for the preparation of dehydroqinghaosu is illustrated in Schematic Diagram (F).

Firstly, qinghao acid is converted by oxygenation into the corresponding carboxylic acid hydroperoxides which are then methylated to give the corresponding new tertiary methyl ester hydroperoxide and the mixture of regioisomeric hydroperoxides.

The major, tertiary methyl ester hydroperoxide is then treated with one or more metal complex catalysts under an oxygen atmosphere and undergoes the new oxygenation-cleavage reaction to give a mixture of the peroxyhemiacetal and dicarbonyl hydroperoxide. The peroxyhemiacetal and dicarbonyl hydroperoxide are then cyclized through acid catalysis to give dehydroqinghaosu.

SCHEMATIC DIAGRAM (F)
Indirect Method for Conversion of Qinghao Acid into Qinghausu.

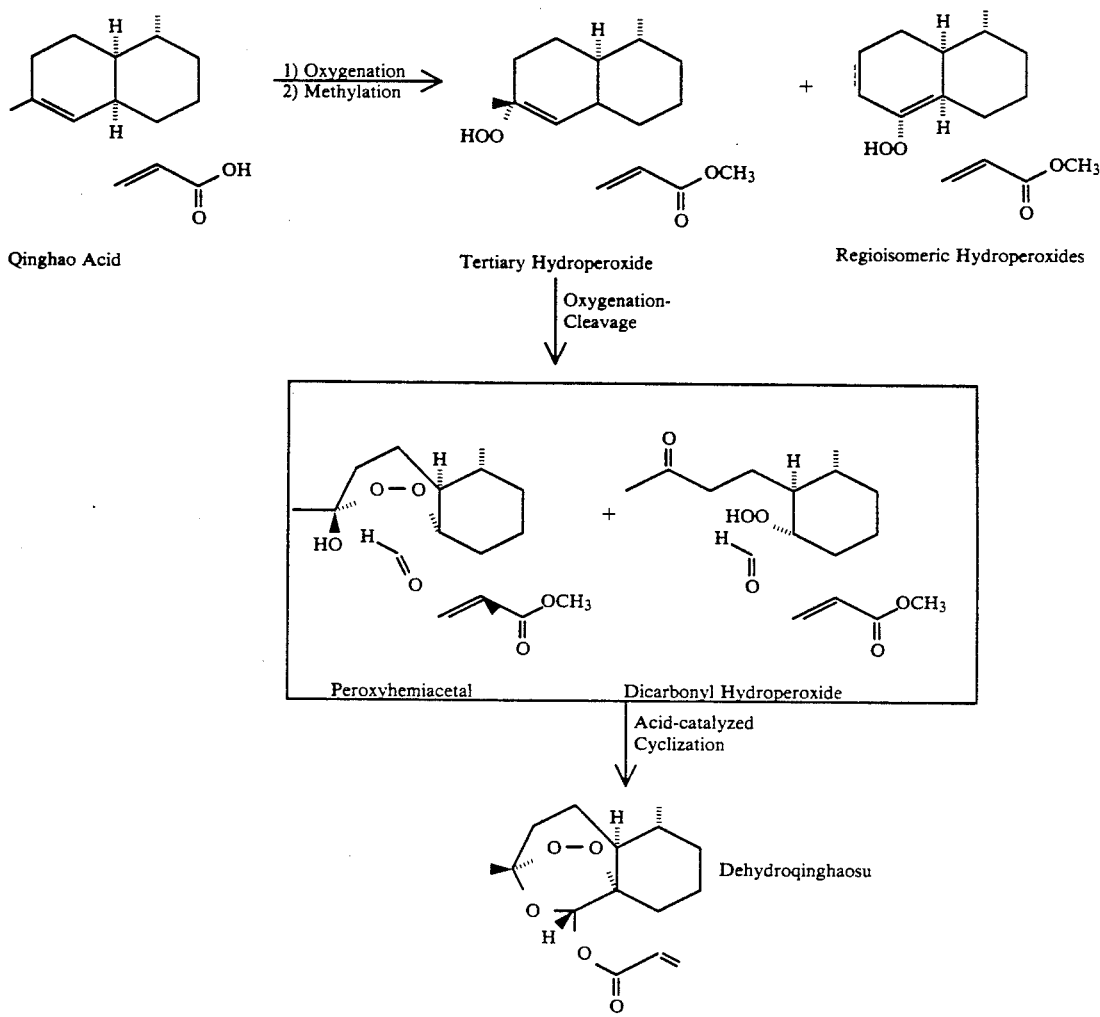

A new methyl peroxyacetal whose formula is given below, also forms as a result of the reaction of the peroxyhemiacetal and hydroperoxide with methanol liberated during the ring closure reaction leading to dehydroqinghaosu.

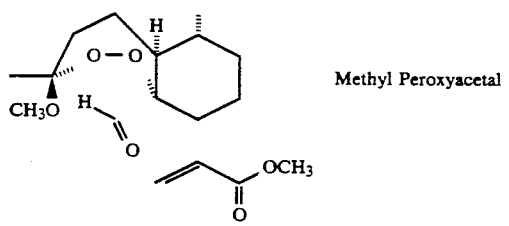

Methyl Peroxyacetal

The dehydroqinghaosu can be converted according to known methods to give qinghaosu or other active antimalarial compounds.

There are many advantages in using the direct method.

Firstly, the direct method involves a "one-pot" reaction and therefore various isolation and/or purification steps are eliminated.

Secondly, the initial methylation step is eliminated. The free acid then acts as an internal acid catalyst in the new oxygenation-cleavage-cyclization process. Thus, the need for an external acid catalyst to effect the final ring closure is not essential, but its presence speeds up the cyclization step and improves the overall yield.

The direct method may also be used to prepare a compound like qinghaosu, but lacking the carbonyl group, and known as deoxoqinghaosu or deoxoartemisinin. The preparation is illustrated in the following Schematic Diagram (G).

SCHEMATIC DIAGRAM (G)
Direct Method for Conversion of Dihydroqinghao Alcohol into Deoxoqinghaosu (Deoxoartemisinin)

-continued
SCHEMATIC DIAGRAM (G)

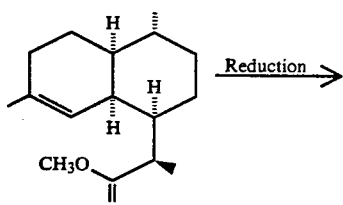

Dihydroqinghao Acid
Methyl Ester

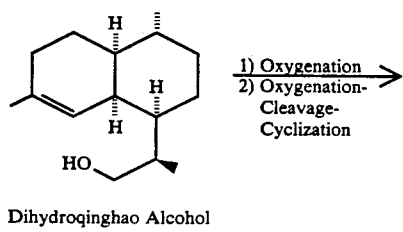

Dihydroqinghao Alcohol

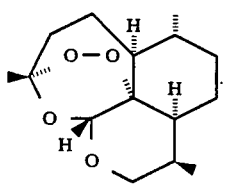

Deoxoqinghaosu

The qinghao acid is first reduced to dihydroqinghao acid, and then this compound is converted by reduction into the known alkene alcohol we name "dihydroqinghao alcohol" via the dihydroqinghao acid methyl ester. The dihydroqinghao alcohol is then converted by oxygenation into the hydroperoxide mixture, which is treated with one or more complex catalysts under an oxygen atmosphere to give deoxoqinghaosu. Deoxoqinghaosu is twice as active as qinghaosu as an antimalarial agent.

The oxygenation step of the present invention is preferably photosensitized oxygenation carried out by treating with singlet oxygen in the presence of Rose Bengal. Preferably, the reaction is carried out in a solvent such as acetonitrile.

Methylation is preferably carried out by treating with diazomethane. This may be prepared from N-nitroso-N-methylurea. The diazomethane is preferably added dropwise in a solution of diethyl ether.

The new oxygenation-cleavage-cyclization and oxygenation-cleavage reactions are typically carried out by treating with one or more oxidizing transition metal complex catalysts such as $Cu(OSO_2CF_3)_2$, Cu(II) propionate, copper(II)2-ethylhexanoate, other copper(II) carboxylate salts, and various iron (III) salts such as $Fe(phenanthroline)_3(PF_6)_3$. Other catalysts that may be used are cobalt(II) and cobalt(III) salts. Preferably, this reaction is carried out in a solvent such as acetonitrile and by treating with any one of the above mentioned catalysts, or with a combination of the copper and iron catalysts. Other suitable solvents include dichloromethane, hexane, ethyl acetate and the like. If the iron catalyst is omitted, then the overall conversion may be somewhat slower. The formation of the cleavage by-products may also be significantly decreased. This results in an increase in the yield of the final product. The new reaction is preferably carried out at a temperature in the range of $-30°$ to $-10°$ C. and preferably allowed to proceed to completion at room temperature.

The acid-catalysed ring closure is generally carried out in the presence of p-toluenesulfonic acid.

These reactions overall constitute the only known synthesis of dehydroqinghaosu, and provide a convenient means of obtaining this potentially commercially valuable compound in large amounts. The only known source of qinghaosu is the annual shrub *Artemisia annua*. Because of the large amount of qinghao acid present is *Artemisia annua* (up to 3%) relative to qinghaosu (up to 0.1%), the above methods will substantially increase the availability of qinghaosu. Moreover, the methods have the potential of providing access to antimalarial agents structurally related to qinghaosu, but possessing enhanced activities.

Specific embodiments of the present invention are illustrated by the following preparative examples. It will be understood, however, that the invention is not confined to the specific limitations set forth in the individual examples.

EXAMPLE 1

Preparation of Qinghaosu (Artemisinin) from Qinghao Acid

Method 1. Direct Conversion

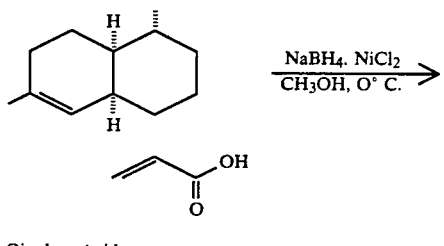

Qinghao Acid

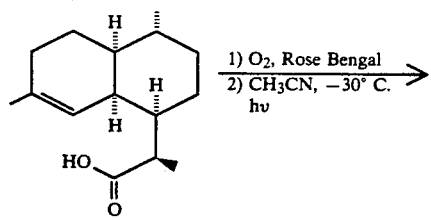

Dihydroqinghao acid

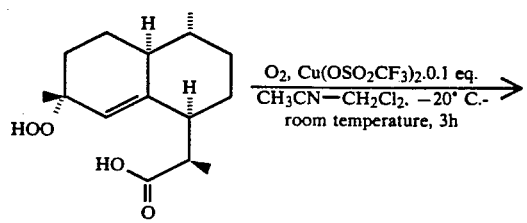

Hydroperoxide

-continued

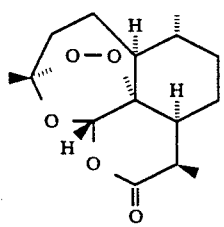

Qinghaosu.

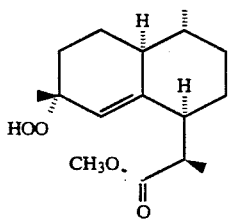

Methyl Ester Hydroperoxide

1) $O_2$, Fe(phen)$_3$(PF$_6$)$_3$, 0.03 eq., Cu(OSO$_2$CF$_3$)$_2$.0.1 eq., CH$_3$CN, 0° C.
2) p-Toluenesulfonic Acid, 0.3 eq., CH$_2$Cl$_2$, 4 h

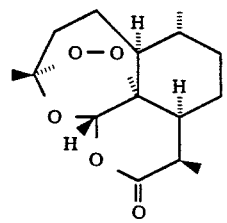

Qinghaosu

Optically-pure qinghao acid (arteannuic or artemisinic acid), obtained from *Artemisia annua*, was reduced with sodium borohydride in methanol according to a literature procedure (Xu, X.-X.:Zhu, J.; Huang, D.-Z.; Zhou, W. S. *Tetrahedron* 1986, 42, 819) to dihydroqinghao acid. This was converted into the hydroperoxide in the following way. A suspension of the acid (289 mg, $1.22 + 10^{-3}$ mol) in acetonitrile (5 ml) containing Rose Bengal (6 mg) was stirred vigorously under an oxygen balloon at $-30°$ C. whilst under irradiation from a tungsten lamp (500 W). After 4 h a clear solution resulted and the oxygenation was complete. In addition to the tertiary hydroperoxide, the photooxygenation also produces a small amount (ca. 18%) of an allylic regioisomer, which does not undergo the subsequent reactions. Without isolation, the mixture was diluted with dichloromethane (20 mL) and the resulting solution was cooled to $-20°$ C. A solution containing Cu(OSO$_2$CF$_3$)$_2$ (44 mg, 0.1 eq.) in acetonitrile (0.5 mL) was added dropwise with stirring. The temperature was held at $-20°$ C. for 1 h and thereafter allowed to rise to room temperature, when the mixture was stirred for a further 2 h. The reaction mixture was poured into water (20 mL) and extracted with ether (2×25 mL). The combined extracts were washed with water (10 mL) and brine (10 mL), and then dried (MgSO$_4$). Evaporation of the solvents left a viscous oil which after flash chromatography on silica gel with ether-light petroleum (1:1) gave crystalline qinghaosu (artemisinin) (165 mg, 48%). $^1$H NMR spectrum (400 MHz, CDCl$_3$) $^1$H NMR spectrum (400 MHz, CDCl$_3$) $\delta 1.002$ (3H, d, $J_{Me,6}=6$ Hz, 6-CH$_3$), 1.03–1.12 (2H,m), 1.209 (3H, d, $J_{Me,9}=7.2$ Hz, 9-CH$_3$), 1.33–1.53 (3H, m), 1.446 (3H, s, 3-CH$_3$), 1.73–1.81 (2H, m), 1.86–1.93 (1H, m), 1.96–2.09 (2 H,m), 2.39–2.48 (1H,m), 3.398 (1H, dddd, $J_{8a,8\alpha}=7.3$, $J_{8a,8\beta}=7.3$, $J_{8a,9}7.3$, $J_{8a,7\alpha}=5.4$ Hz, H8a), 5.862 (1H, s, H-12).

Addition of 0.1 eq. of p-toluenesulfonic acid to the reaction mixture 0.5 h after addition of the metal catalyst resulted in a more rapid reaction, and formation of the qinghaosu in higher yield.

EXAMPLE 2

Method 2. Indirect Conversion

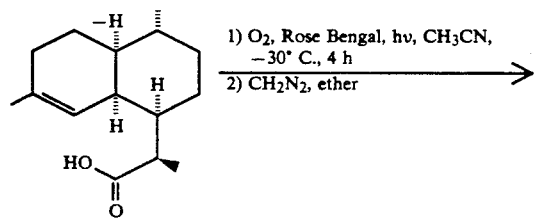

Dihydroqinghao acid

1) $O_2$, Rose Bengal, hv, CH$_3$CN, $-30°$ C., 4 h
2) CH$_2$N$_2$, ether

The dihydroqinghao acid (103.1 mg, $4.36 \times 10^{-4}$ mol) was photooxygenated as described above. The solvent was removed under vacuum from the reaction mixture to leave the crude mixture of the carboxylic acid hydroperoxide and its regioisomer in a ratio of 4.5:1, according to $^1$H NMR analysis. The mixture was dissolved in diethyl ether (17.5 mL), and treated dropwise with a solution of diazomethane, prepared form N-nitroso-N-methylurea (350 mg) in diethyl ether (17.5 mL) at 0° C. Addition of the diazomethane solution was continued until TLC analysis indicated complete conversion of the free carboxylic acid hydroperoxide into the methyl esters. The mixture was treated with 5% aqueous acetic acid to decompose excess diazomethane. The resulting mixture was washed with water, aqueous sodium hydrogen carbonate and then brine. The ether solution was dried (MgSO$_4$), and then evaporated to dryness to give a viscous oil. The major (tertiary) hydroperoxide, a known compound (Jung, M.; El Sohly, H. N.; Groom. E. M. *J. Org. Chem.* 1986, 51, 819) was isolated by flash chromatography on silica gel with diethyl ether - light petroleum (3:7) as the second fraction (72.2 mg, 70%) The hydroperoxide (72.2 mg. $2.55 \times 10^{-4}$ mol) in acetonitrile (4 mL) was treated with Fe(phenanthroline)$_3$(PF$_6$)$_3$ (0.03 eq.) in acetonitrile (0.9 mL) followed by Cu(OSO$_2$CF$_3$)$_2$ (0.1 eq.) in acetonitrile (0.5 mL) at 0° C. After 30 min. the reaction mixture was worked up as described previously to give a crude product, which was dissolved in dichloromethane (20 mL). p-Toluene-sulfonic acid monohydrate (15 mg, $7.65 \times 10^{-5}$ mol) was added, and the resulting mixture was stirred at room temperature for 4 h. It was then poured onto an ether-water mixture. The ether layer was separated, and the aqueous layer was extracted with ether. The combined ether layers were processed in the usual way to give the crude product, which was submitted to flash chromatography on silica gel with ether-light petroleum (6:4) to give qinghaosu as fine needles (20:1 mg, 28% from the hydroperoxide).

EXAMPLE 3

Preparation of Dehydroqinghaosu (Artemisitene) from Qinghao Acid

Method 1. Direct Conversion

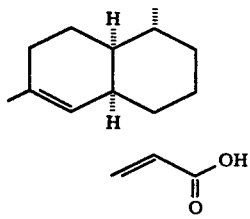

Qinghao Acid

1) O$_2$, Rose Bengal, hν, CH$_3$CN, −30° C., 2 h
2) O$_2$, Fe(phen)$_3$(PF$_6$)$_3$, 0.002 eq., Cu(OSO$_2$CF$_3$)$_2$.0.1 eq. CH$_3$CN, −20° C. - room temperature, 3 h

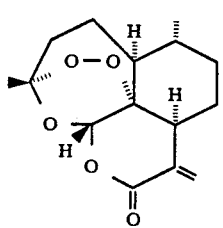

Dehydroqinghaosu

Qinghao acid (32 mg, $1.37 \times 10^{-4}$ mol) in acetonitrile (1.5 mL) containing Rose Bengal (ca. 0.5 mg) at −30° C. under oxygen was converted into the free carboxylic acid hydroperoxides corresponding to the methyl ester hydroperoxides described below. Without isolation, the mixture was diluted with dichloromethane (5.4 mL) and the resulting solution was cooled to −20° C. A solution containing Fe(phenanthroline)$_3$(PF$_6$)$_3$ (0.002 eq.) and Cu(OSO$_2$CF$_3$)$_2$ (0.1 eq.) in acetonitrile (0.6 mL) was added dropwise with stirring. The temperature was held at −20° C. for 1 h and thereafter allowed to rise to room temperature, when the mixture was stirred for a further two hours. By-products of the reaction, not formed in method 2 below, as detected by thin-layer chromatography of the reaction mixture, were the keto-aldehydes. The

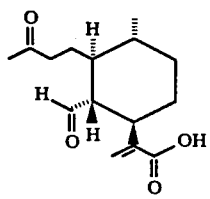 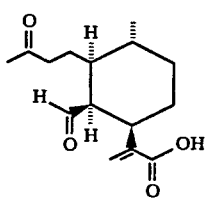

Keto-aldehydes reaction mixture was poured into water (10 mL) and extracted with ether (2×25 mL). The combined extracts were washed with water (10 mL) and brine (10 mL); and then dried (MgSO$_4$). Evaporation of the solvents left a viscous oil which was submitted to flash chromatography on silica gel with ether-light petroleum (1:1) to give crystalline dehydroqinghaosu (artemisitene) 5 (14.4 mg, 38%).

EXAMPLE 4

Method 2. Indirect Conversion a) Oxygenation of Qinhao Acid.

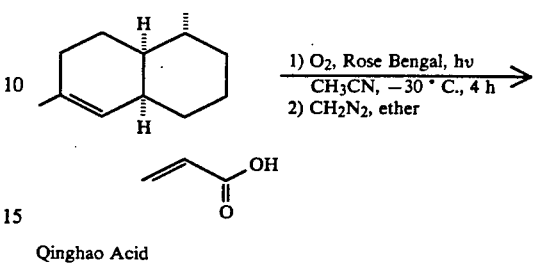

Qinghao Acid

1) O$_2$, Rose Bengal, hν CH$_3$CN, −30° C., 4 h
2) CH$_2$N$_2$, ether

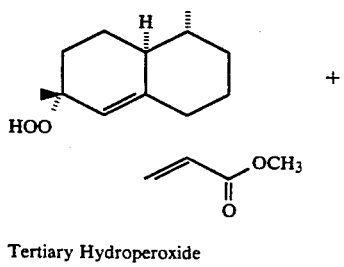

Tertiary Hydroperoxide

+

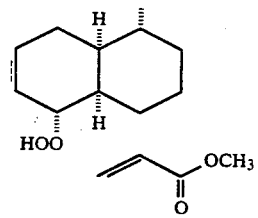

Regioisomeric Hydroperoxides

A suspension of qinghao acid (arteannuic or artemisinic acid) (338.2 mg, $1.44 \times 10^{-3}$ mol) in acetonitrile (35 mL) containing Rose Bengal (6 mg) was stirred vigorously under an oxygen balloon at −30° C. whilst under irradiation from a tungsten lamp (500 W). After 4 h a clear solution resulted and the oxygenation was complete. The solvent was removed under vacuum to leave the crude mixture of the carboxylic acid hydroperoxides in a ratio of 4.5:1, according to $^1$H NMR analysis. The mixture was dissolved in diethyl ether (17.5 mL), and treated dropwise with a solution of diazomethane, prepared form N-nitroso-N-methyl-urea (350 mg) in diethyl ether (17.5 mL) at 0° C. Addition of the diazomethane solution was continued until TLC analysis indicated complete conversion of the free carboxylic acid hydroperoxides into the methyl esters. The mixture was treated with 5% aqueous acetic acid to decompose excess diazomethane. The resulting mixture was washed with water, aqueous sodium hydrogen carbonate and then brine. The ether solution was dried (MgSO$_4$), and then evaporated to dryness to give a viscous oil. The major (tertiary) hydroperoxide, a new compound was isolated by flash chromato-graphy on silica gel with diethyl ether - light petroleum (3:7) as the second fraction (287.4 mg, 71%). $^1$H NMR spectrum (400 MHz, CDCl$_3$) δ0.981 (3H, d, $J_{Me,6}=6.4$ Hz, 6-CH$_3$), 1.18–1.27 (1H, m, H 6), 1.209 (3H, s, 3-CH$_3$), 1.27–1.38 (2H,m), 1.514 (1H, dddd, $J_{gem}=12.5$, $J_8$ β,8a=12.5, J8β,7β3.5 Hz, H8β), 1.527 (1H, dddd, J=13.0, J=7.3, J=3.0, J=0.8 Hz, H 5a?), 1.72-1.79 (1H, m), 1.804 (1H, dddd, J$_{gem}$=12.3, J$_{8a,8a}$3.5, J$_{8a7a}$3.5, J$_{8a,7β}$=3.5 Hz, H8a), 1.834 (1H, dddd, J=12.6. J=3.3, J=3.3 Hz), 1.971 (1H, ddd, J=13.1, J=10.8. J=3.5 Hz), 2.048 (1H, dddd, J=13.1, J=7.5, H=5.8 Hz), 3.141 (1H, br d, J$_{8a,8β}$=12.6 Hz, H8a), 3.741 (3H, s, OCH$_3$), 4.978 (1H, ddd, J$_{12,8a}$=1.6, J=1.6, J=1.6, J=0.8 Hz, H12), 5.581 (1H, dd, J$_{gem}$=1.1, J$_{methylidene,8a}$=1.1 Hz, H methylidene), 6.362 (1H, d, J$_{gem}$=1.1 Hz, H methylidene), 7.575 (1H, br s, W$_{h/2}$ 2.0 Hz, OOH).

b) Cleavage-oxygenation to give the peroxyhemiacetal and dicarbonyl hydroperoxide

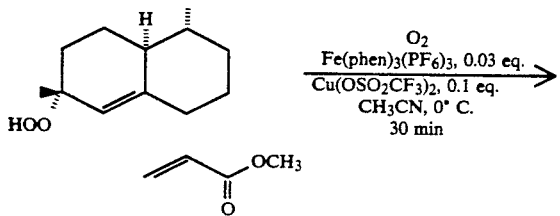

Tertiary Hydroperoxide

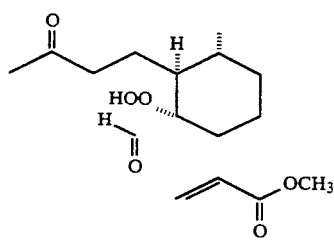

Peroxyhemiacetal

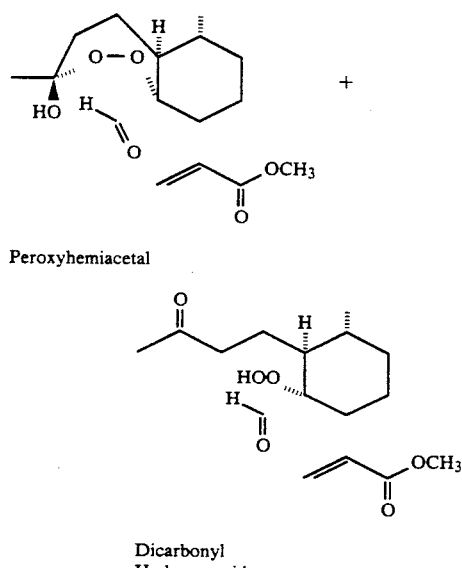

Dicarbonyl Hydroperoxide

The tertiary hydroperoxide (106.3 mg, 3.78×10$^{-4}$ mol) in acetonitrile (5 mL) was treated with Fe(-phenanthroline)$_3$ (PF$_6$)$_3$ (0.03 eq. in 0.6 mL acetonitrile) and then with Cu(OSO$_2$CF$_3$)$_2$ (0.1 eq. in 0.5 mL acetonitrile) at 0° C. under an oxygen atmosphere.

The reaction mixture was stirred for 30 min with slow warming toward room temperture, and then poured onto a mixture of ether and water. The aqueous phase was extracted with ether and the combined extracts were washed with water until colourless, and then with brine. The organic phase was dried (MgSO$_4$), and the solvent was removed under reduced pressure to leave a viscous oil, analysis of which by $^1$H NMR spectroscopy indicated that it consisted of predominantly the oxygenation products. This was isolated by flash chromatography on silica gel with ether-light petroleum (6:4) as an unstable viscous oil (62.5 mg, 53%). Prolonged exposure of the mixture of oxygenation products to silica gel resulted in decomposition to a more polar product. The oxygenation products were an equilibrium mixture of the peroxyhemiacetal and the free dicarbonyl hydroperoxide. Both are new compounds. IR ν$_{max}$ (CHCl$_3$)3580-3450 (br s), 3450-3130 (br s), 3001 (m), 2956 (s), 2940 (s), 2872 (m), 2854 (m), 1732 (s) (C=O), 1714 (vs) (C=O), 1627 (w), 1443 (s), 1285 (m), 1167 (s), 1100 )m), 961 (m) cm$^{-1}$. $^1$H NMR (400 MHz, CDCl$_3$) peroxyhemiacetal δ 0.933 (3H, d, J$_{Me}$,66.4 Hz, 6-CH$_3$), 0.86-1.20 (2$^r$, m), 1.217 (3H, s, 3-CH $_3$), 1.26-1.39 (3H, m), 1.56-2.24 (4H, m), 2.32-2.45 (1H, m, H6), 2.94-3.01 (1H, dd, J$_{8a,8β}$=9.6, J$_{8a,8a}$7.1 Hz, H8a), 3.804 (3H, s, OCH$_3$), 5.468 (1H, s, methylidene), 6.260 (1H, s, methylidene), 9.617 (1H, d, J$_{12,5a}$=2.5 Hz, H12); dicarbonyl hydroperoxide δ 0.991 (3H, d, J$_{Me}$,66.4 Hz, 6-CH$_3$), 0.96-1.20 (2H, m), 1.26-1.39 (3H, m), 1.56-2.24 (4H, m), 2.141 (3H, s, 3-CH$_3$), 2.585 (1H, ddd, J$_{gem}$=17.6, J$_{4,5}$=9.3, J$_{4,5}$=6.1 Hz, H4), 2.713 (1H, ddd, J$_{gem}$=17.6, J$_{4,5}$=9.3, J$_{4,5}$=6.1 Hz, H4), 3.197 (1 H, dd, J$_{8a,8β}$=13.3 J$_{8a,8a}$=3.5 Hz, H8a), 3.840 (3H, s, OCH$_3$), 5.597 (1H, s, methylidene), 6.383 (1H, s, methylidene), 9.340 (1H, dd, J=1.5, J=1.5 Hz, H12 ), 10399 (1H, s, OOH). Preirradiation at δ 9.6 (H12, peroxyhemiacetal) resulted in enhancements at δ5.47 (methylidene, peroxyhemiacetal) of 1% and at δ3.80 (OCH$_3$) of 1%. $^{13}$C NMR spectrum (100 MHz, CDCl$_3$), δ 20.049, 20.369, 20.568, 22.070, 22.515, 23.513, 26.986, 27.256, 27.790, 29.644, 29.644, 29.886, 32.078, 33.777, 34.672, 35.144, 40.701, 41.657, 43.407, 43.862, 46.348, 52.278 (OCH$_3$, peroxyhemiacetal) 52.933 (OCH$_3$, dicarbonyl hydroperoxide), 58.546, 92.29 (C12a, dicarbonyl hydroperoxide), 92.31 (C12a, peroxyhemiacetal), 105.90 (C3, dicarbonyl hydroperoxide), 125.02 (methylidene C, peroxyhemiacetal), 129.01 (methylidene C, dicarbonyl hydroperoxide), 139.55 (C9, dicarbonyl hydroperoxide), 139.70 (C9, peroxyhemiacetal), 166.20 (C10, peroxyhemiacetal), 170.41 (C10, dicarbonyl hydroperoxide), 201.39 (C12, peroxyhemiacetal), 203.14 (C12, dicarbonyl hydroperoxide), 209.14 (C3, dicarbonyl hydroperoxide).

c) Tandem cyclization of peroxyhemiacetal and dicarbonyl hydroperoxide to dehydroqinghaosu (artemisitene).

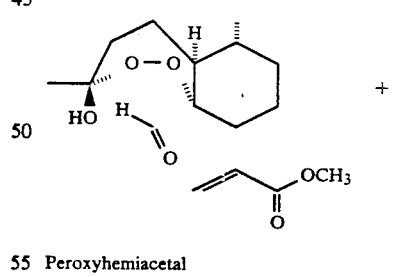

Peroxyhemiacetal

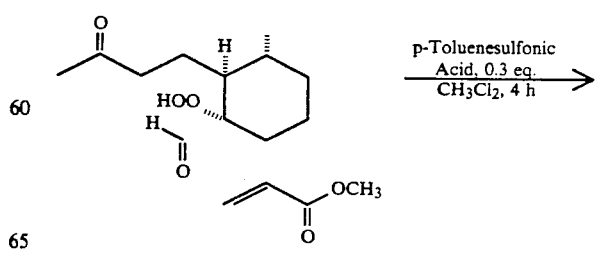

Dicarbonyl Hydroperoxide

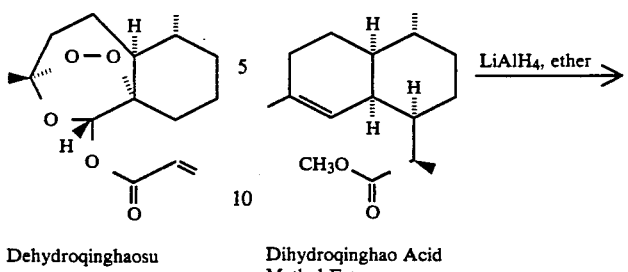

Dehydroqinghaosu

The mixture of the peroxyhemiacetal and dicarbonyl hydroperoxide was prepared as described above from the tertiary hydroperoxide (110.3 mg, 3.92×10⁻⁴ mol). The mixture of products was immediately dissolved in dichloromethane (5 mL) and treated with p-toluenesulfonic acid monohydrate (0.3 eq.). The resulting mixture was stirred for 4 h at room temperature, and then poured onto an ether-water mixture. The ether layer was separated, and the aqueous layer was extracted with ether. The combined ether layers were processed as described above to give a viscous oil, which upon flash chromatography on silica gel with ether-light petroleum (6:4) gave dehydroqinghaosu (artemisitine) as fine needles (47.9 mg, 43% from the tertiary hydroperoxide, or 30% from qinghao acid), m.p. 164°–166° C., a known compound. ¹H NMR spectrum (400 MHz, CDCl₃) δ 1.017 (3H, d, $J_{Me,6}$=5.9 Hz, 6-CH₃), 1.15–1.27 (1H,m), 1.42–1.63 (3H, m, including H8), 1.43–1.48 (1H, m, H6), 1.459 (3H, s, 3-CH₃), 1.72–1.80 (2H, m, including H8), 1.94–2.01 (1H, m), 2.04–2.10 (1H,m), 2.37–2.45 (1H,m), 2.550 (1H, dd, $J_{8a,8\beta}$=13.6, $J_{8a,8\alpha}$=4.5 Hz, H8a), 5.672 (1H, dd, $J_{gem}$=1.1, $J_{methylidene,8a}$=1.1 Hz, methylidene), 5.995 (1H, s, H12), 6.570 (1H, dd, $J_{gem}$=1.2, $J_{methylidene,8a}$=0.5 Hz, H methylidene).

Also formed was the methyl peroxyacetal (17.8 mg, 14%) from the reaction of the peroxyhemiacetal and dicarbonyl hydroperoxide with the methanol formed during the ring closure reaction leading to dehydroqinghaosu.

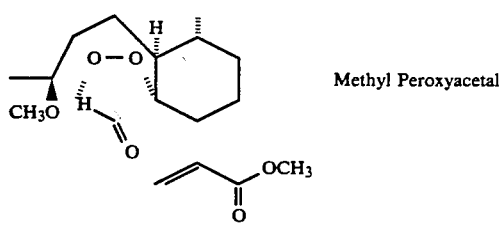

Methyl Peroxyacetal

EXAMPLE 5

Conversion of Dihydroqinghao Alcohol into Deoxoqinghaosu

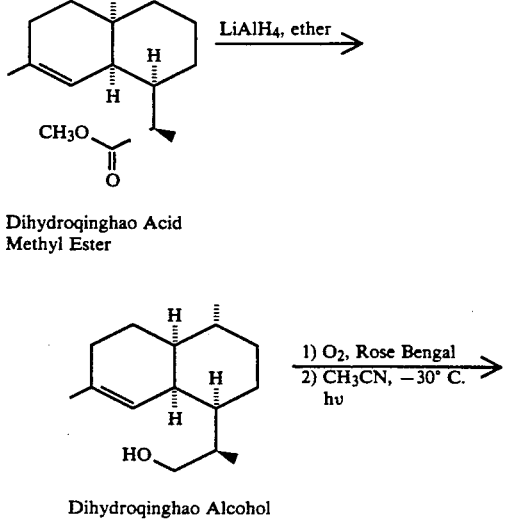

Dihydroqinghao Acid Methyl Ester

Dihydroqinghao Alcohol

Alcohol Hydroperoxide

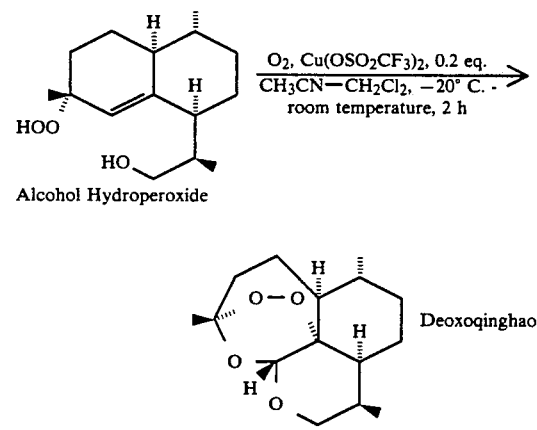

Deoxoqinghaosu

Dihydroqinghao alcohol (arteannuinol) was obtained by the reduction of dihydroqinghao acid methyl ester with lithium aluminium hydride in ether according to a literature procedure (Ye, B; Wu, Y. -L. *Tetrahedron* 1989, 45, 7287). Dihydroqinghao alcohol (43.9 mg, 1.97×10⁻⁴ mol) in acetonitrile (2.5 ml) containing Rose Bengal (ca. 0.5 mg) was then irradiated under oxygen at −30° C. for 2 h to give a hydroperoxide mixture containing predominantly the tertiary hydroperoxide. The mixture was diluted with dichloromethane, cooled to −15° C. and then treated with Cu(OSO₂CF₃)₂ (0.2 eq)in acetonitrile (0.4 ml) for 1 h 45 min, with gradual warming to room temperature. The reaction mixture was quenched with water and then worked up as previously described to give a viscous oil. This was submitted to flash chromatography on silica gel with ether-light petroleum (2:3) to give deoxoqinghaosu as a white solid (19 mg, 36% from dihydroqinghao alcohol). Spectroscopic data is in agreement with that reported in the literature (Jung, M.; Li., X.; Bustos, D. A.; ElSohly, H. N.; McChesney, J. D., *Tetrahedron Lett.* 1989, 30, 5973)

EXAMPLE 6

Conversion of Model Compound into Peroxyacetal Lactone

Method 1. Direct Conversion

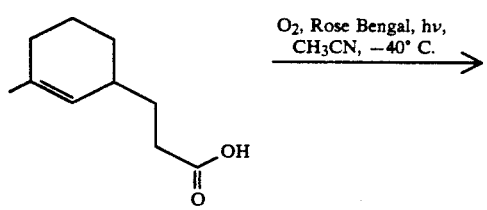

a

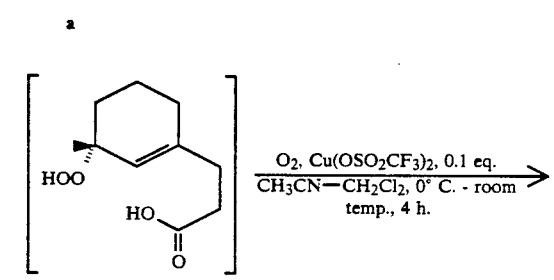

b

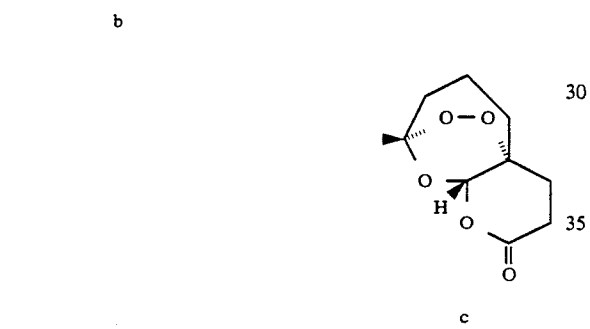

c

The compound a, a new compound, was obtained from a known mixture of the corresponding methyl ester and a double bond regioisomer of the ester (Claus, P. K.; Vierhapper, F. W.; Willer, R. L. *J. Org. Chem.*, 1977, 42, 4016), through hydrolysis of the mixture with lithium hydroxide in aqueous dimethoxyethane, and separation of the resulting mixture of carboxylic acids through an iodolactonization procedure (Corey, E. J.; Wright, S. W., *J. Org. Chem.*, 1988, 53, 5980). The acid a (134 mg, $7.97 \times 10^{-4}$ mol) in acetonitrile (4mL) containing Rose Bengal (3 mg) under oxygen was irradiated as described below for qinghao acid to give the racemic hydroperoxide b and double bond regioisomers in a ratio of 1:1. The mixture was diluted with dichloromethane (16 mL) and then treated with Cu(OSO$_2$CF$_3$)$_2$ (0.1 eq.) in acetonitrile (0.2 mL) under oxygen at 0° C. This resulted in the immediate conversion of compound b into a polar intermediate. The other regioisomers of compound b did not appear to react under these conditions. The reaction mixture was allowed to warm to room temperature and was stirred for 4 h. The mixture was poured onto water and extracted with ether as described below for the preparation of qinghaosu to give a viscous oil. This was submitted to flash chromatography with ether-light petroleum 7:3 to give the racemic compound c as a colourless gum (51 mg, 30%).

EXAMPLE 7

Method 2. Indirect Conversion

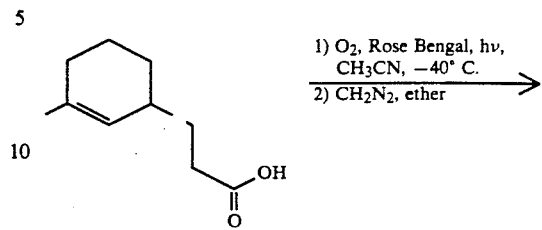

a

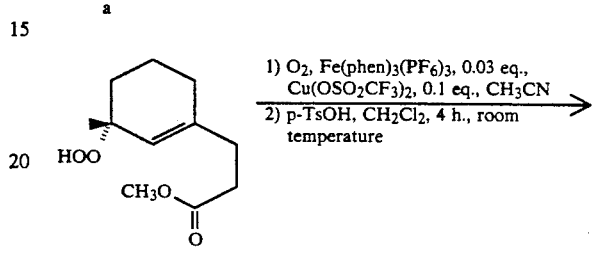

d

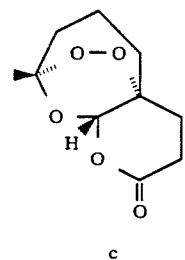

c

The acid a (110 mg, $6.54 \times 10^{-3}$ mol) was converted into the racemic hydroperoxide b and its mixture of regioisomers as described above. The crude mixture of hydroperoxides was dissolved in ether and treated with an excess of diazomethane at 0° C. The racemic ester hydroperoxide d (96 mg, 45%) was isolated by flash chromatography with ether-light petroleum 3:7 of the mixture of ester hydroperoxides obtained after methylation. The hydroperoxide d (96 mg, $4.48 \times 10^{-4}$ mol) in acetonitrile (5 mL) under oxygen was treated with Fe(phen)$_3$(PF$_6$)$_3$ (0.03 eq.) in acetonitrile (1 mL) followed by Cu(OSO$_2$CF$_3$)$_2$ (0.1 eq.) in acetonitrile (0.5 mL) at 0° C. After 30 min, the reaction mixture was worked up to leave the crude product mixture consisting of a peroxy hemiacetal and hydroperoxide analogous to those described for the indirect conversion of qinghao acid into dehydroqinghaosu (artemisitene) described below. A solution of the mixture in dichloromethane (20 mL) containing p-toluenesulfonic acid (26 mg, $1.34 \times 10^{-4}$ mol) was stirred for 4 h at room temperature. Workup as previously described gave a viscous oil which after purification by flash chromatography with ether-light petroleum 7:3 gave the racemic peroxyacetal lactone c (48 mg, 50% from a).

We claim:

1. A process for converting qinghao acid into qinhaosu comprising
   i) reducing qinghao acid to give dihydroqinghao acid of formula

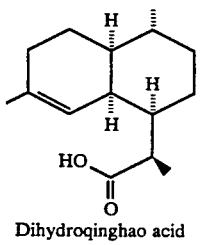

Dihydroqinghao acid ii) oxygenating dihydroqinghao acid to give the corresponding hydroperoxides and without isolation
iii) oxgenating in the presence of one or more oxidising metal catalysts to give qinghaosu.

2. A process according claim 1 wherein the catalyst is one or more transition metal complex catalysts selected from Cu(OSO₂CF₃)₂, Cu(II) propionate, Cu(II) 2-ethylhexanoate, other Cu(II) carboxylate salts, Fe(phenanthroline)₃(PF₆)₃ and other iron (III) salts.

3. A process according to claim 1 or 2 further comprising the addition of a protic acid or lewis acid catalyst following step iii).

4. A process for converting qinghao acid into qinghaosu comprising
   i) reducing qinghao acid to give dihydroqinghao acid;
   ii) oxygenation of dihydroqinghao acid followed by methylation to give the methylester hydroperoxide of the formula

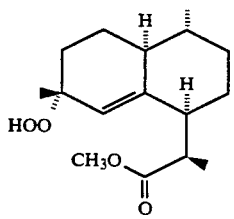

iii) oxygenation in the presence of one or more oxidizing metal catalysts to give intermediate products of formulae

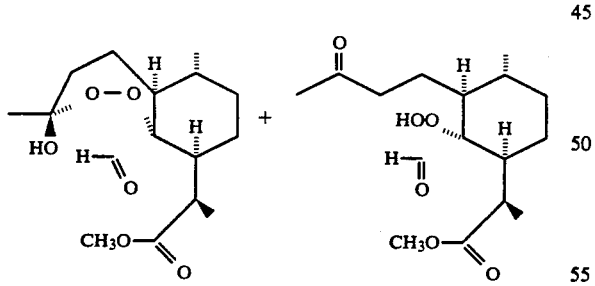

and with or without isolation
   iv) treatment with protic or Lewis acid catalyst to give qinghaosu.

5. A process according to claim 4 wherein the metal catalyst is one or more transition metal complex catalysts selected from Cu(OSO₂CF₃)₂, Cu(II) propionate, Cu(II) 2-ethylhexanoate, other Cu(II) carboxylate salts, Fe(phenanthroline)₃(PF₆)₃ and other iron (III) salts.

6. A process for converting qinghao acid into dehydroqinghaosu comprising
   i) oxygenation to give the intermediate hydroperoxide ii) oxygenation in the presence of one or more metal catalysts to give the desired product of formula

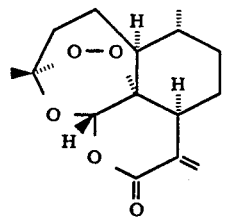

7. A process according to claim 6 wherein the catalyst is one or more transition metal complex catalysts selected from Cu(OSO₂CF₃)₂, Cu(II) propionate, Cu(II) 2-ethylhexanoate, other Cu(II) carboxylate salts, Fe(phenanthroline)₃(PF₆)₃ and other iron (III) salts.

8. A process according to claim 6 or 7 further comprising the addition of a protic acid or Lewis acid catalyst following step ii).

9. A process for converting qinghao acid into dehydroqinghaosu comprising
   i) oxygenation of qinghao acid into the hydroperoxides followed by methylation to give a compound of formula

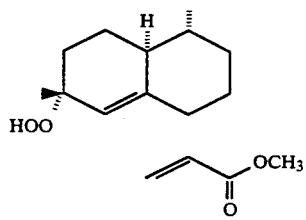

Tertiary Hydroperoxide ii) oxygenation in the presence of one or more oxidizing metal catalysts to give intermediate products of formulae

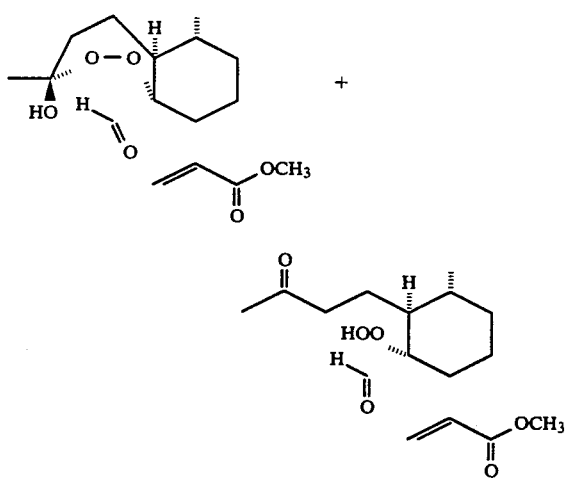

and with or without isolation
   iii) treatment with protic or Lewis acid catalyst to give dehydroqinghaosu.

10. A process according to claim 9 wherein the metal catalyst is one or more transition metal complex catalysts selected from Cu(OSO$_2$CF$_3$)$_2$, Cu(II) propionate, Cu(II) 2-ethylhexanoate, other Cu(II) carboxylate salts, Fe(phenanthroline)$_3$(PF$_6$)$_3$ and other iron (III) salts.
11. A compound of formula
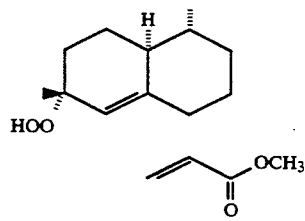
12. A compound of formula
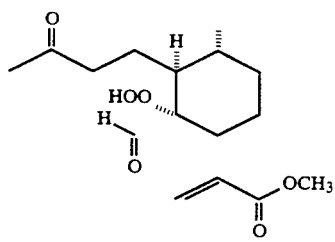
13. A compound of formula
14. A compound of formula
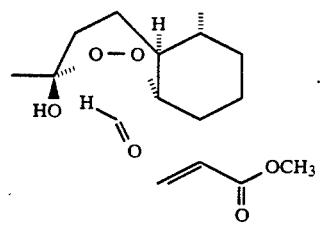
15. A compound of formula
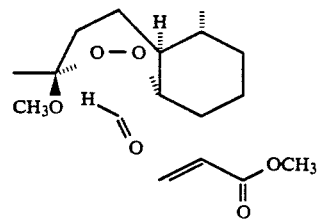
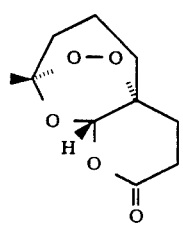
* * * * *

UNITED STATES PATENT AND TRADEMARK OFFICE
CERTIFICATE OF CORRECTION

PATENT NO. : 5,310,946
DATED : Haynes et al.
INVENTOR(S) : May 10, 1994

It is certified that error appears in the above-indentified patent and that said Letters Patent is hereby corrected as shown below:

Cover Page, in the Abstract, line 24, delete [an y] and insert --any--.

Column 2, line 33, after "arylalkyl" insert --;--.

Column 5, lines 1-44, delete

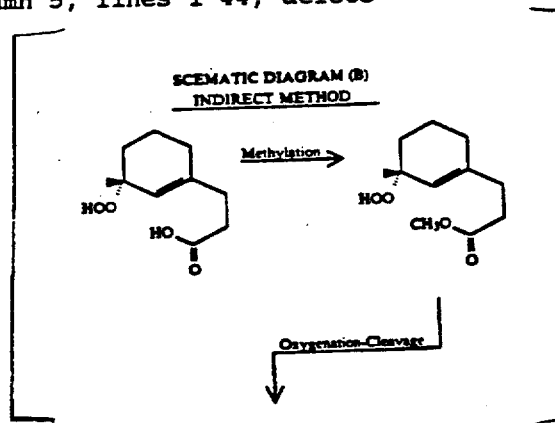

UNITED STATES PATENT AND TRADEMARK OFFICE
CERTIFICATE OF CORRECTION

PATENT NO. : 5,310,946
DATED : Haynes et al.
INVENTOR(S) : May 10, 1994

It is certified that error appears in the above-indentified patent and that said Letters Patent is hereby corrected as shown below:

Continued

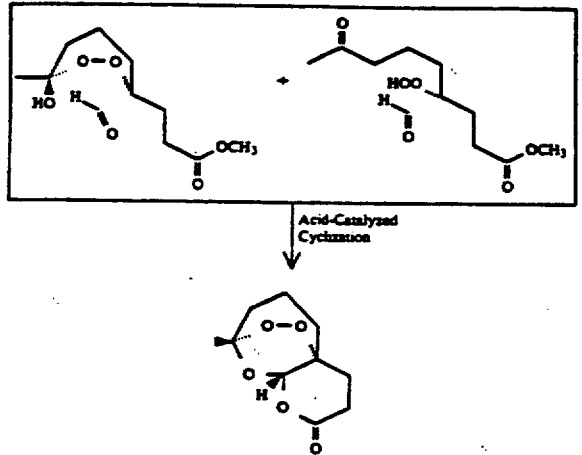

NB In this Scheme one enantiomer only of each chiral compound is depicted. There is also produced an equal amount of the other enantiomer in each case.

and insert

-- -- INDIRECT METHOD

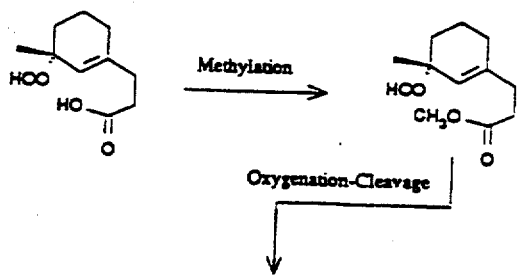

Oxygenation-Cleavage

UNITED STATES PATENT AND TRADEMARK OFFICE
CERTIFICATE OF CORRECTION

PATENT NO. : 5,310,946
DATED : Haynes et al.
INVENTOR(S) : May 10, 1994

It is certified that error appears in the above-indentified patent and that said Letters Patent is hereby corrected as shown below:

Continued

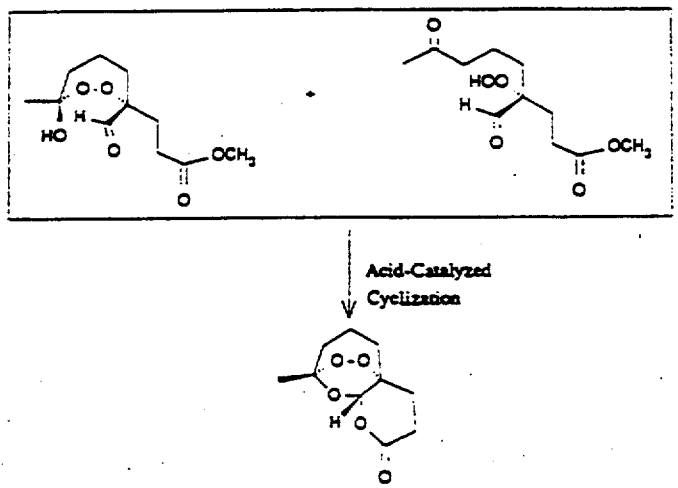

NB: In this Scheme one enantiomer only of each chiral compound is depicted. There is also produced an equal amount of the other enantiomer in each case.

Column 7, lines 33-42, delete

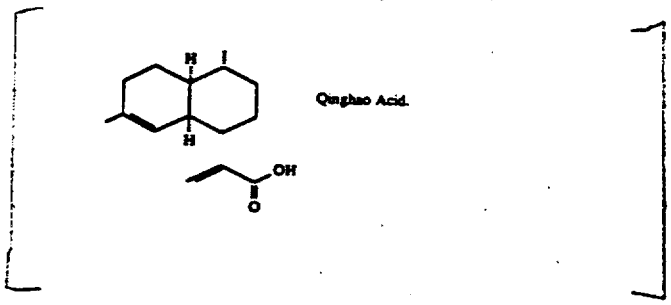

UNITED STATES PATENT AND TRADEMARK OFFICE
CERTIFICATE OF CORRECTION

PATENT NO. : 5,310,946
DATED : May 10, 1994
INVENTOR(S) : Haynes et al.

It is certified that error appears in the above-indentified patent and that said Letters Patent is hereby corrected as shown below:

and insert

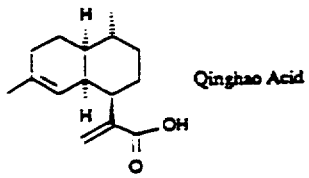

Qinghao Acid

Column 7, lines 55-65, delete

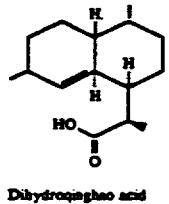

Dihydroqinghao acid and insert

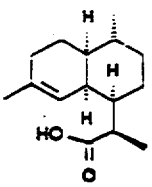

Dihydroqinghao acid

UNITED STATES PATENT AND TRADEMARK OFFICE
CERTIFICATE OF CORRECTION

PATENT NO. : 5,310,946
DATED : May 10, 1994
INVENTOR(S) : Haynes et al.

It is certified that error appears in the above-indentified patent and that said Letters Patent is hereby corrected as shown below:

Column 8, lines 25-39, delete

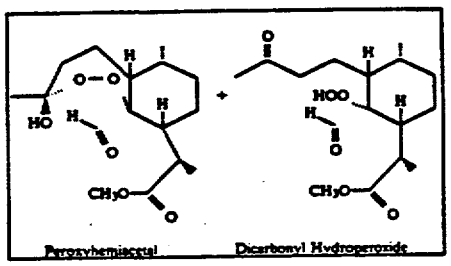

and insert

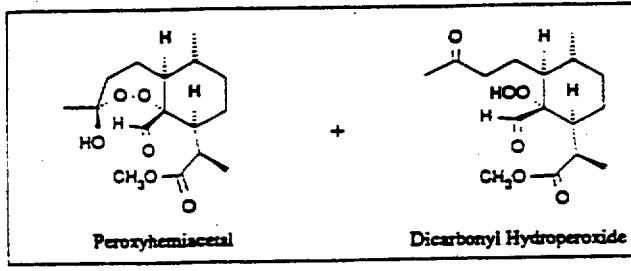

Column 8, lines 55-65, delete

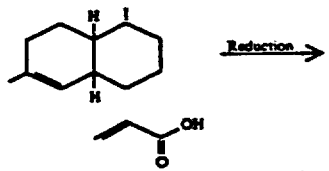

UNITED STATES PATENT AND TRADEMARK OFFICE
CERTIFICATE OF CORRECTION

PATENT NO. : 5,310,946
DATED : Haynes et al.
INVENTOR(S) : May 10, 1994

Page 6 of 29

It is certified that error appears in the above-indentified patent and that said Letters Patent is hereby corrected as shown below:

and insert

-- --

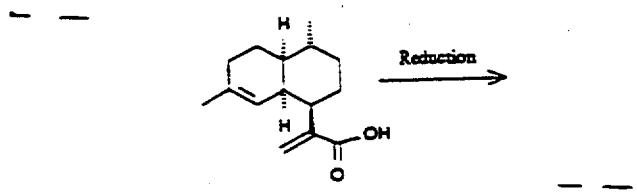

-- --

Column 9 and 10, Schematic Diagram (D), delete

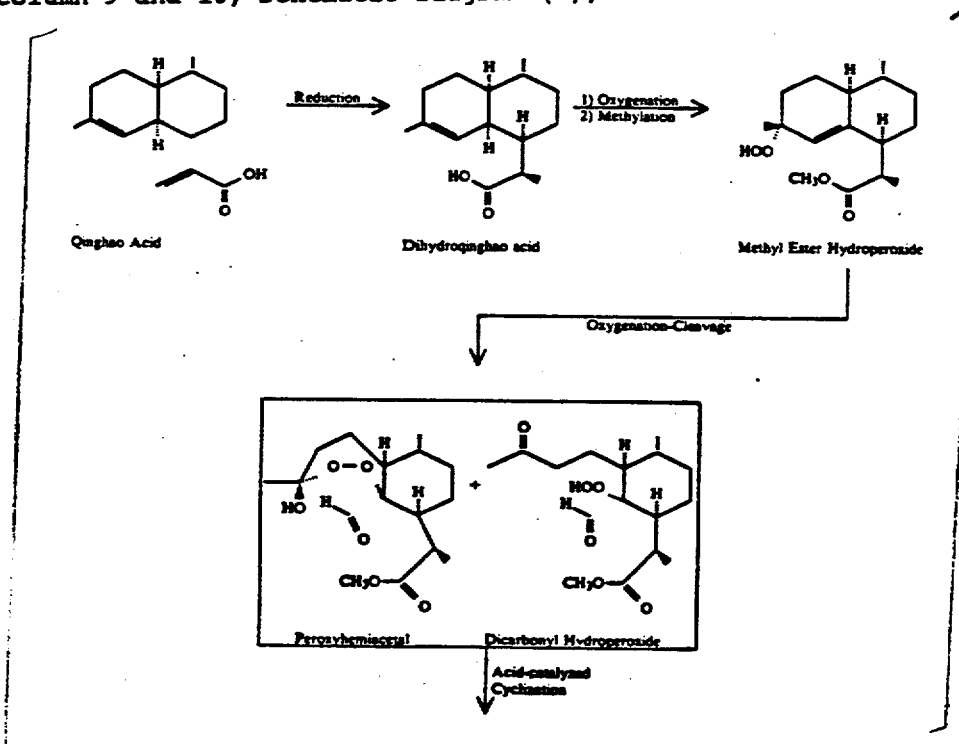

UNITED STATES PATENT AND TRADEMARK OFFICE
CERTIFICATE OF CORRECTION

PATENT NO. : 5,310,946
DATED : Haynes et al.
INVENTOR(S) : May 10, 1994

Page 7 of 29

It is certified that error appears in the above-indentified patent and that said Letters Patent is hereby corrected as shown below:

and insert

—  — Indirect Method for Conversion of Qinghao Acid into Qinghaosu.

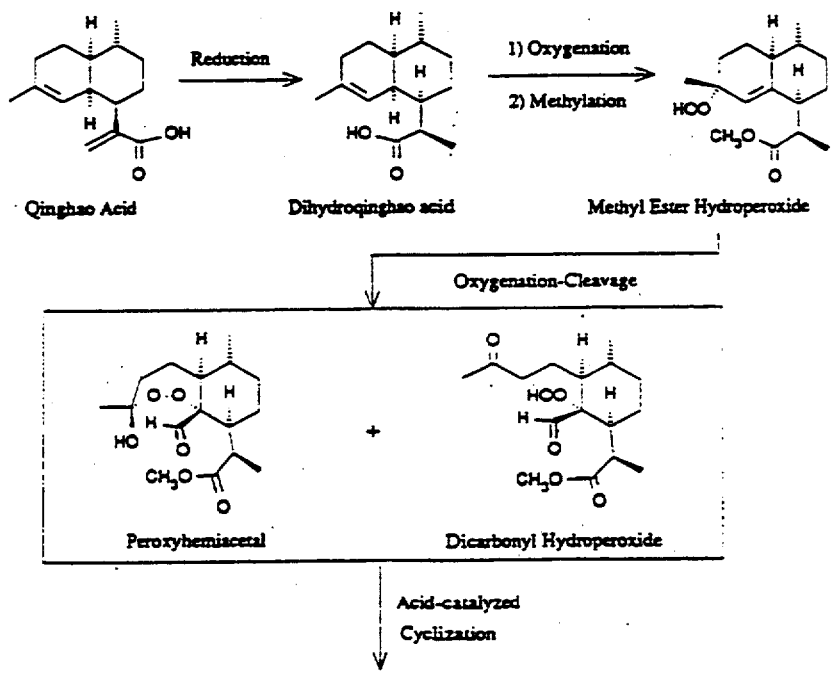

— —

UNITED STATES PATENT AND TRADEMARK OFFICE
CERTIFICATE OF CORRECTION

PATENT NO. : 5,310,946
DATED : Haynes et al.
INVENTOR(S) : May 10, 1994

Page 8 of 29

It is certified that error appears in the above-indentified patent and that said Letters Patent is hereby corrected as shown below:

Column 10, lines 5-14, delete

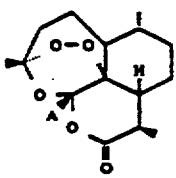

and insert

-- 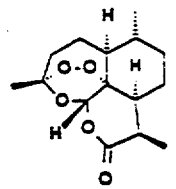 --

UNITED STATES PATENT AND TRADEMARK OFFICE
CERTIFICATE OF CORRECTION

PATENT NO. : 5,310,946
DATED : Haynes et al.
INVENTOR(S) : May 10, 1994

It is certified that error appears in the above-indentified patent and that said Letters Patent is hereby corrected as shown below:

Column 11, lines 43-65, delete

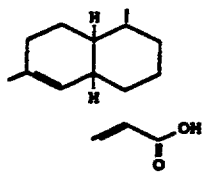

Qinghao Acid

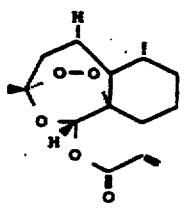

Dehydroqinghaosu and insert

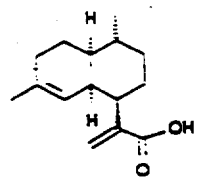

Qinghao Acid

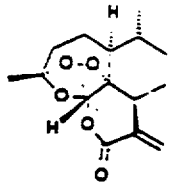

UNITED STATES PATENT AND TRADEMARK OFFICE
CERTIFICATE OF CORRECTION

PATENT NO. : 5,310,946
DATED : Haynes et al.
INVENTOR(S) : May 10, 1994

It is certified that error appears in the above-indentified patent and that said Letters Patent is hereby corrected as shown below:

Columns 13 and 14, lines 3-44, delete

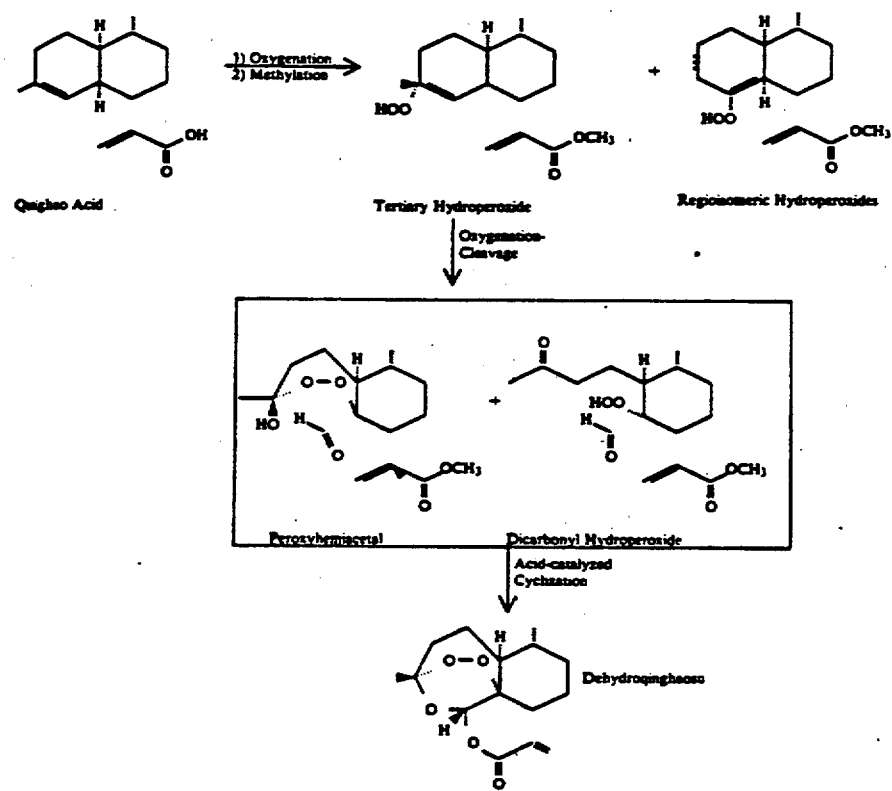

UNITED STATES PATENT AND TRADEMARK OFFICE
CERTIFICATE OF CORRECTION

PATENT NO. : 5,310,946
DATED : May 10, 1994
INVENTOR(S) : Haynes et al.

It is certified that error appears in the above-indentified patent and that said Letters Patent is hereby corrected as shown below:

and insert

-- 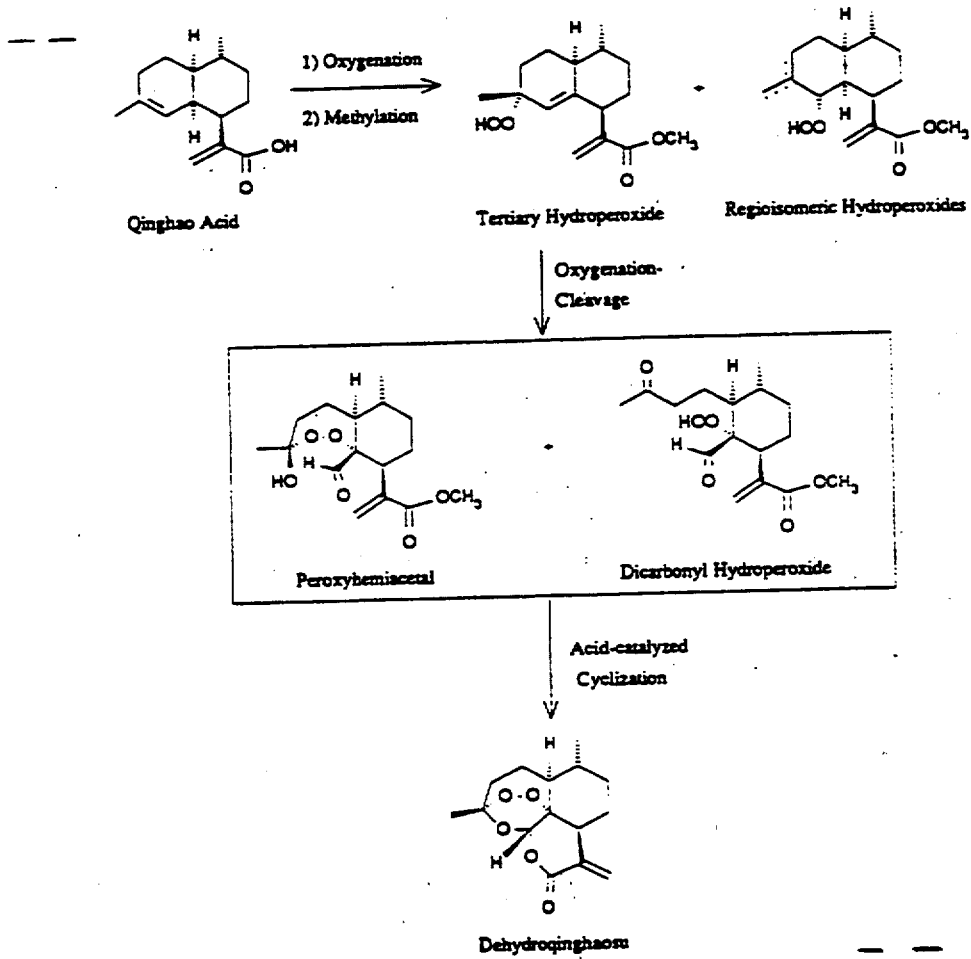 --

UNITED STATES PATENT AND TRADEMARK OFFICE
CERTIFICATE OF CORRECTION

PATENT NO. : 5,310,946
DATED : Haynes et al.
INVENTOR(S) : May 10, 1994

It is certified that error appears in the above-indentified patent and that said Letters Patent is hereby corrected as shown below:

Column 13, lines 48-59, delete

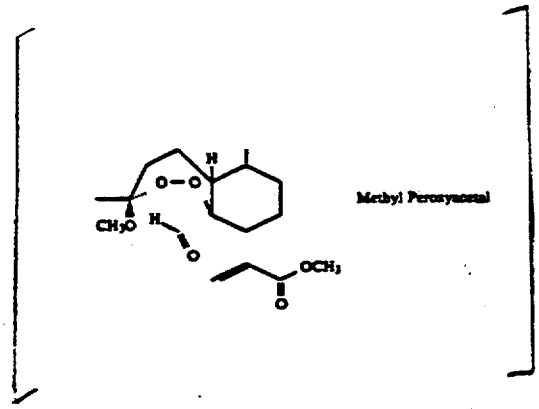

and insert

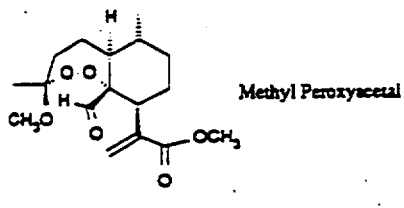

UNITED STATES PATENT AND TRADEMARK OFFICE
CERTIFICATE OF CORRECTION

PATENT NO. : 5,310,946
DATED : Haynes et al.
INVENTOR(S) : May 10, 1994

Page 13 of 29

It is certified that error appears in the above-indentified patent and that said Letters Patent is hereby corrected as shown below:

Column 16, lines 35-44, delete

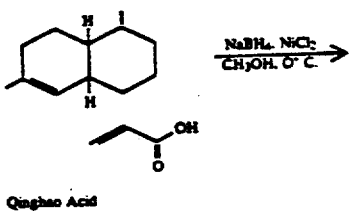

Qinghao Acid and insert

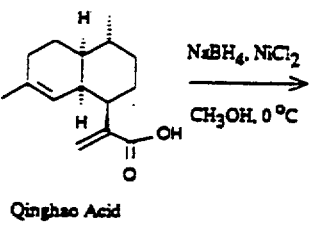

Qinghao Acid

Column 17, line 19, delete [1.22 + $10^{-3}$] and insert --1.22 X $10^{-3}$--.

UNITED STATES PATENT AND TRADEMARK OFFICE
CERTIFICATE OF CORRECTION

PATENT NO. : 5,310,946  
DATED : Haynes et al.  
INVENTOR(S) : May 10, 1994

Page 14 of 29

It is certified that error appears in the above-indentified patent and that said Letters Patent is hereby corrected as shown below:

Column 17, lines 57-65, delete

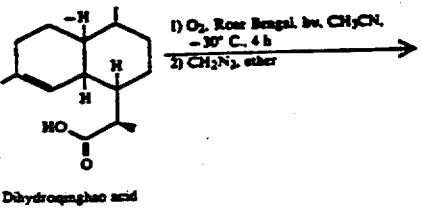

and insert

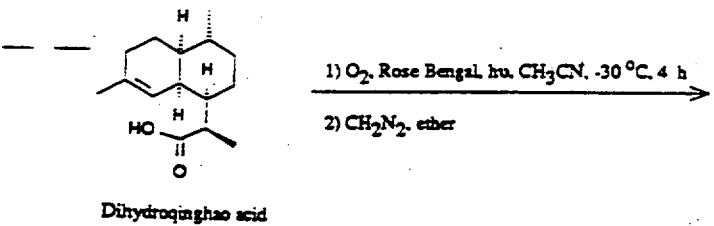

Column 19, lines 9-20, delete

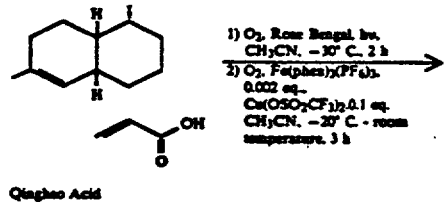

UNITED STATES PATENT AND TRADEMARK OFFICE
CERTIFICATE OF CORRECTION

PATENT NO. : 5,310,946
DATED : Haynes et al.
INVENTOR(S) : May 10, 1994

Page 15 of 29

It is certified that error appears in the above-indentified patent and that said Letters Patent is hereby corrected as shown below:

and insert

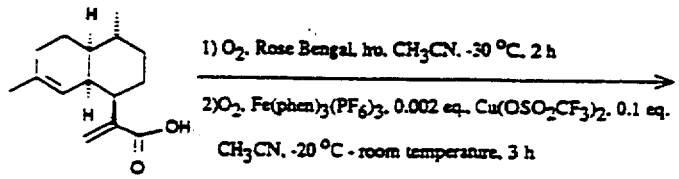

Qinghao Acid

Column 20, lines 5-39, delete a) Oxygenation of Qinhao Acid.

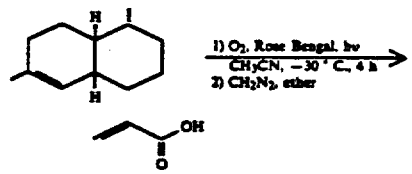

Qinghao Acid

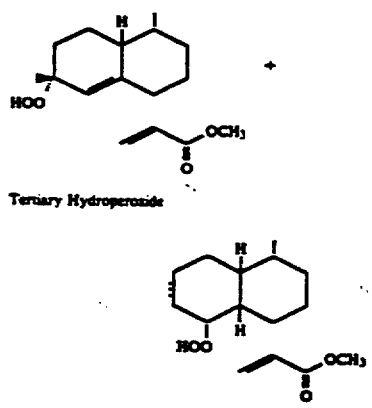

Tertiary Hydroperoxide

Regioisomeric Hydroperoxides

UNITED STATES PATENT AND TRADEMARK OFFICE
CERTIFICATE OF CORRECTION

PATENT NO. : 5,310,946
DATED : Haynes et al.
INVENTOR(S) : May 10, 1994

It is certified that error appears in the above-indentified patent and that said Letters Patent is hereby corrected as shown below:

and insert

-- *a) Oxygenation of Qinghao Acid.*

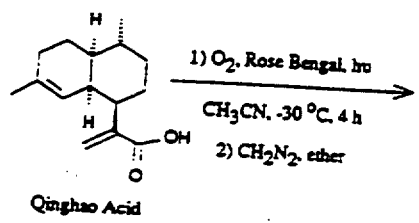

Qinghao Acid

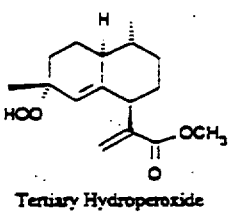

Tertiary Hydroperoxide

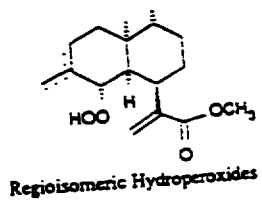

Regioisomeric Hydroperoxides --

UNITED STATES PATENT AND TRADEMARK OFFICE
CERTIFICATE OF CORRECTION

PATENT NO. : 5,310,946
DATED : Haynes et al.
INVENTOR(S) : May 10, 1994

It is certified that error appears in the above-indentified patent and that said Letters Patent is hereby corrected as shown below:

Column 21, lines 15-47, delete

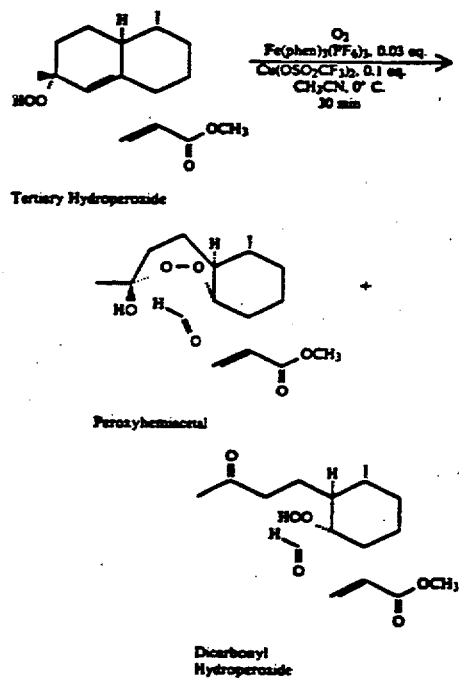

UNITED STATES PATENT AND TRADEMARK OFFICE
CERTIFICATE OF CORRECTION

PATENT NO. : 5,310,946
DATED : Haynes et al.
INVENTOR(S) : May 10, 1994

It is certified that error appears in the above-indentified patent and that said Letters Patent is hereby corrected as shown below:

and insert

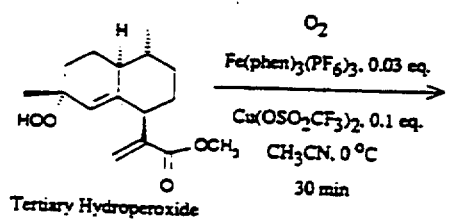
Tertiary Hydroperoxide

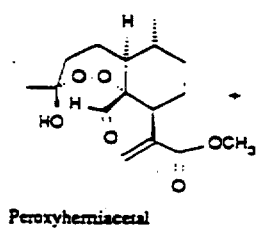
Peroxyhemiacetal

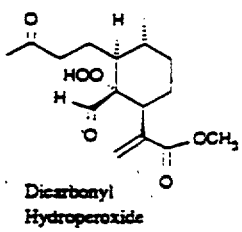
Dicarbonyl Hydroperoxide

UNITED STATES PATENT AND TRADEMARK OFFICE
CERTIFICATE OF CORRECTION

PATENT NO. : 5,310,946
DATED : May 10, 1994
INVENTOR(S) : Haynes et al.

It is certified that error appears in the above-indentified patent and that said Letters Patent is hereby corrected as shown below:

Column 22, lines 45-65, delete

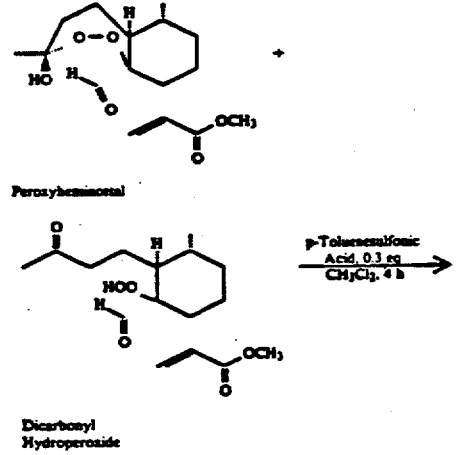

and insert

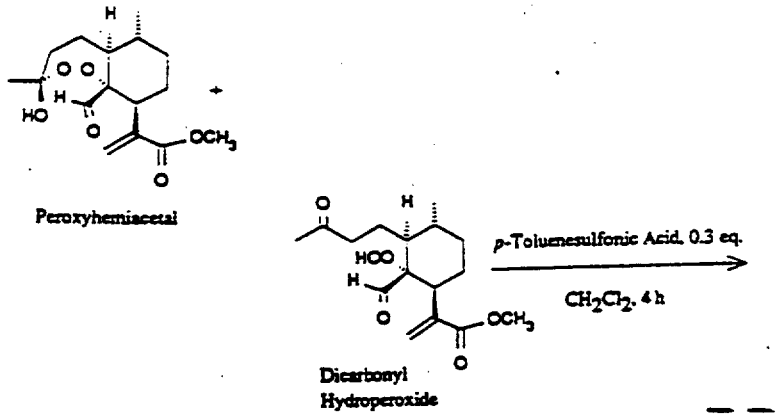

UNITED STATES PATENT AND TRADEMARK OFFICE
CERTIFICATE OF CORRECTION

PATENT NO. : 5,310,946
DATED : May 10, 1994
INVENTOR(S) : Haynes et al.

It is certified that error appears in the above-indentified patent and that said Letters Patent is hereby corrected as shown below:

Column 23, lines 1-14, delete

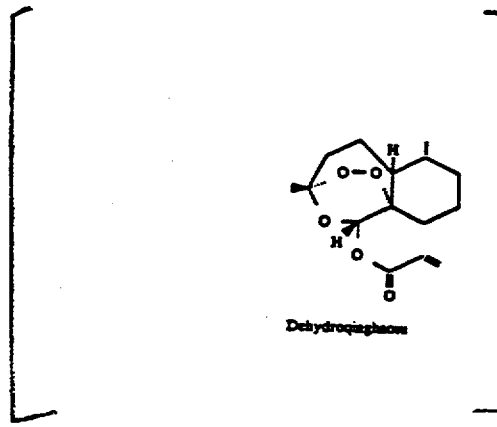

and insert

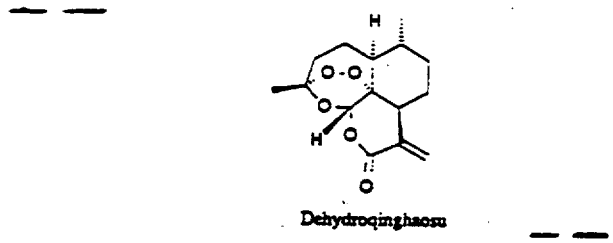

UNITED STATES PATENT AND TRADEMARK OFFICE
CERTIFICATE OF CORRECTION

PATENT NO. : 5,310,946
DATED : Haynes et al.
INVENTOR(S) : May 10, 1994

It is certified that error appears in the above-indentified patent and that said Letters Patent is hereby corrected as shown below:

Column 23, lines 54-63, delete

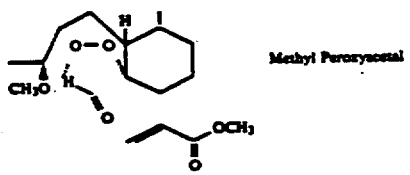

and insert

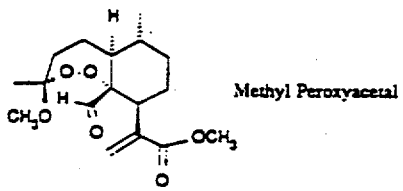

UNITED STATES PATENT AND TRADEMARK OFFICE
CERTIFICATE OF CORRECTION

PATENT NO. : 5,310,946
DATED : May 10, 1994
INVENTOR(S) : Haynes et al.

It is certified that error appears in the above-indentified patent and that said Letters Patent is hereby corrected as shown below:

Column 27, lines 45-55, delete

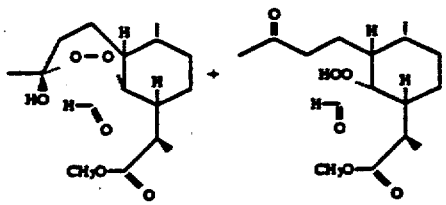

and insert

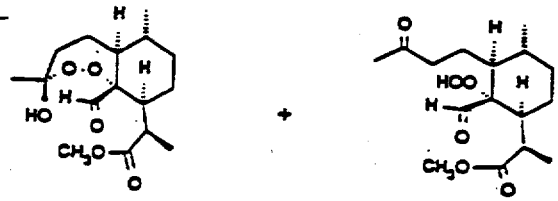

UNITED STATES PATENT AND TRADEMARK OFFICE
CERTIFICATE OF CORRECTION

PATENT NO. : 5,310,946

DATED : Haynes et al.

INVENTOR(S) : May 10, 1994

It is certified that error appears in the above-indentified patent and that said Letters Patent is hereby corrected as shown below:

Column 28, lines 30-39, delete

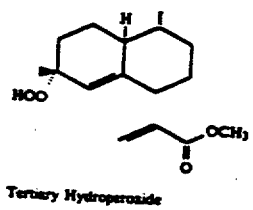

and insert

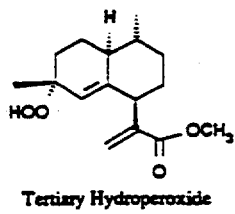

UNITED STATES PATENT AND TRADEMARK OFFICE
CERTIFICATE OF CORRECTION

PATENT NO. : 5,310,946
DATED : Haynes et al.
INVENTOR(S) : May 10, 1994

It is certified that error appears in the above-indentified patent and that said Letters Patent is hereby corrected as shown below:

Column 28, lines 45-60, delete

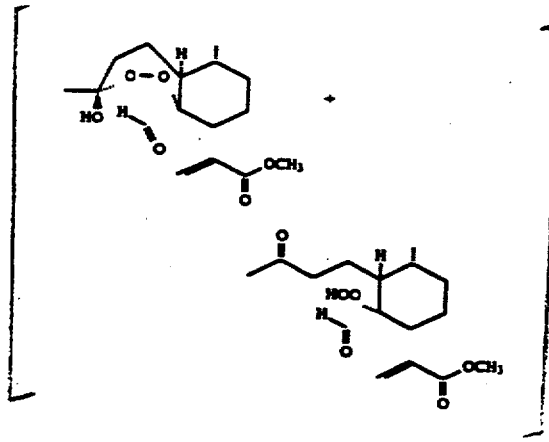

and insert

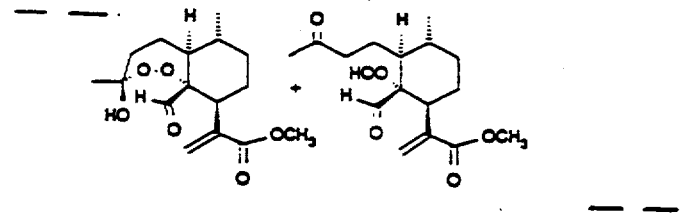

UNITED STATES PATENT AND TRADEMARK OFFICE
CERTIFICATE OF CORRECTION

PATENT NO. : 5,310,946
DATED : Haynes et al.
INVENTOR(S) : May 10, 1994

It is certified that error appears in the above-indentified patent and that said Letters Patent is hereby corrected as shown below:

Column 29, lines 10-40, delete

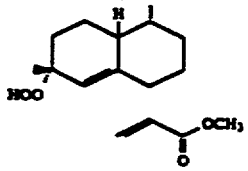

12. A compound of formula

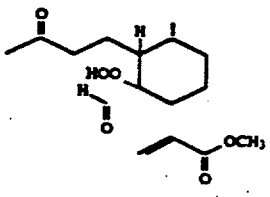

13. A compound of formula and insert

-- 11. A compound formula

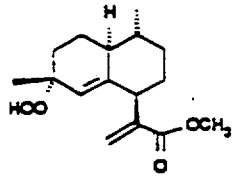

UNITED STATES PATENT AND TRADEMARK OFFICE
CERTIFICATE OF CORRECTION

PATENT NO. : 5,310,946
DATED : Haynes et al.
INVENTOR(S) : May 10, 1994

It is certified that error appears in the above-indentified patent and that said Letters Patent is hereby corrected as shown below:

12. A compound of formula

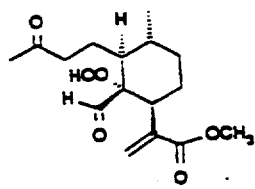

13. A compound of formula

Column 30, lines 5-35, delete

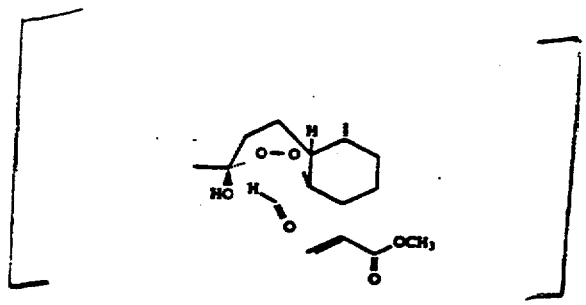

UNITED STATES PATENT AND TRADEMARK OFFICE
CERTIFICATE OF CORRECTION

PATENT NO. : 5,310,946
DATED : May 10, 1994
INVENTOR(S) : Haynes et al.

It is certified that error appears in the above-indentified patent and that said Letters Patent is hereby corrected as shown below:

Continued

[
14. A compound of formula

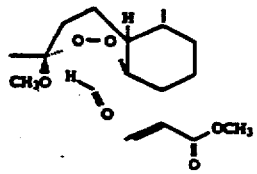

15. A compound of formula

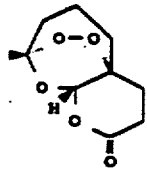

]

and insert

-- 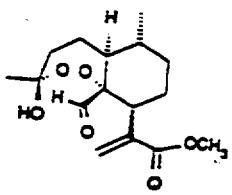 --

UNITED STATES PATENT AND TRADEMARK OFFICE
CERTIFICATE OF CORRECTION

PATENT NO. : 5,310,946
DATED : Haynes et al.
INVENTOR(S) : May 10, 1994

It is certified that error appears in the above-indentified patent and that said Letters Patent is hereby corrected as shown below:

Continued

14. A compound of formula

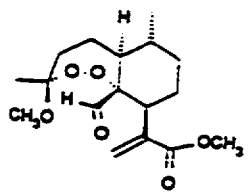

UNITED STATES PATENT AND TRADEMARK OFFICE
CERTIFICATE OF CORRECTION

PATENT NO. : 5,310,946
DATED : Maynes et al
INVENTOR(S) : May 10, 1994

It is certified that error appears in the above-indentified patent and that said Letters Patent is hereby corrected as shown below:

15. A compound of formula

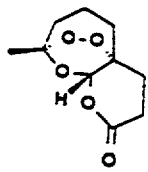

* * * * *

Signed and Sealed this

Fifteenth Day of August, 1995

Attest:

BRUCE LEHMAN

Attesting Officer    Commissioner of Patents and Trademarks